United States Patent
Goulait et al.

(10) Patent No.: US 6,637,079 B1
(45) Date of Patent: Oct. 28, 2003

(54) MULTI-LAYER FEMALE COMPONENT FOR REFASTENABLE FASTENING DEVICE AND METHOD OF MAKING THE SAME

(75) Inventors: David J. K. Goulait, Cincinnati, OH (US); Dennis A. Thomas, Forest Park, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/441,503

(22) Filed: May 15, 1995

Related U.S. Application Data

(62) Division of application No. 08/139,363, filed on Oct. 19, 1993, which is a continuation-in-part of application No. 08/078,712, filed on Jun. 17, 1993, which is a division of application No. 07/703,426, filed on May 20, 1991, now abandoned, which is a division of application No. 07/668,817, filed on Mar. 7, 1991, now Pat. No. 5,230,851, which is a continuation of application No. 07/305,354, filed on Jan. 31, 1989, now abandoned.

(51) Int. Cl.[7] .............................................. A44B 18/00
(52) U.S. Cl. ............................ 24/450; 24/306; 24/442; 24/448; 24/452
(58) Field of Search ........................ 24/450, 451, 452, 24/442, 306, 443, 444, 445, 446, 447, 448, 449

(56) References Cited

U.S. PATENT DOCUMENTS

| | | | |
|---|---|---|---|
| 2,039,312 A | 5/1936 | Goldman | 154/46 |
| 2,496,820 A | 2/1950 | Smith | 155/184 |
| 2,625,161 A | 1/1953 | Johnson | 128/290 |
| 2,991,843 A | 7/1961 | Bell, Jr. | 183/51 |
| 3,005,219 A | 10/1961 | Miller | 15/98 |
| 3,080,688 A | 3/1963 | Politzer | 51/185 |
| 3,085,309 A | 4/1963 | Olson | 28/79 |

(List continued on next page.)

FOREIGN PATENT DOCUMENTS

| | | | |
|---|---|---|---|
| DE | 3533881 A1 | 9/1984 | ........... A41B/13/04 |
| EP | 0258015 * | 3/1988 | ................... 24/442 |
| EP | 0 341 993 A1 | 11/1989 | ........... A44B/18/00 |
| EP | 0 381 087 A1 | 8/1990 | ........... A44B/18/00 |
| EP | 0 409 315 A1 | 1/1991 | ........... B32B/31/08 |
| EP | 0 187 725 B1 | 3/1991 | ........... B32B/27/12 |
| FR | 2432108 | 7/1978 | ........... A44B/21/00 |
| FR | 2586558 | 3/1987 | ........... A61F/13/16 |
| GB | 1140576 | 1/1969 | ........... A44B/21/00 |
| GB | 1299897 | 12/1972 | ........... A44B/21/00 |
| JP | 2-88015 | 3/1990 | ........... A47G/27/02 |
| TW | 34231 | 12/1980 | |
| TW | 48288 | 1/1983 | |

*Primary Examiner*—Victor Sakran
(74) *Attorney, Agent, or Firm*—David M. Weirich; Ken K. Patel; Steve W. Miller

(57) ABSTRACT

The present invention provides a female component for engaging a complementary hook component in a refastenable fastening device. The female component of the present invention is capable of engaging a hook component that has flexible, resilient individual hook elements. The female component comprises at least two, and preferably three zones or layers. Each zone has certain of the desired individual characteristics for entangling and holding the hooks of the mating hook component. These include a first zone for admitting and engaging at least some of the hooks of the complementary hook component (the "entanglement" zone), a second zone for providing space for the hooks to occupy after they have been admitted by the entanglement zone (referred to as the "spacing" zone), and a backing adjacent to the spacing zone for providing a foundation for the entanglement and spacing zones. The present invention also provides a fastening device having a hook fastening component and a female component that comprises the multi-layer female component of the present invention. The present invention also relates to disposable articles and more particularly to a disposable diaper having such an improved fastening device.

5 Claims, 11 Drawing Sheets

U.S. PATENT DOCUMENTS

| | | | |
|---|---|---|---|
| 3,094,330 A | 6/1963 | Smith .......................... 273/54 |
| 3,171,820 A | 3/1965 | Volz .......................... 260/2.5 |
| 3,176,364 A | 4/1965 | Dritz .......................... 24/213 |
| 3,214,323 A | 10/1965 | Russell et al. .............. 161/148 |
| 3,226,751 A | 1/1966 | Lemelson .................... 15/118 |
| 3,255,749 A | 6/1966 | Smithers |
| 3,266,113 A | 8/1966 | Flanagan, Jr. ................. 24/204 |
| 3,266,841 A | 8/1966 | Altman ...................... 297/220 |
| 3,277,547 A | 10/1966 | Billarant ..................... 24/204 |
| 3,302,232 A | 2/1967 | Wasiloff et al. .......... 15/230.17 |
| 3,319,307 A | 5/1967 | Mariforio .................... 24/204 |
| 3,327,708 A | 6/1967 | Sokolowski ................ 128/256 |
| 3,405,430 A | 10/1968 | Sidelman .................... 24/204 |
| 3,469,289 A | 9/1969 | Whitacre ................. 24/205.17 |
| 3,484,330 A | 12/1969 | Sokolowski et al. .......... 161/59 |
| 3,490,107 A | 1/1970 | Brumlik ..................... 24/204 |
| 3,494,006 A | 2/1970 | Brumlik ..................... 24/204 |
| 3,665,921 A | 5/1972 | Stumpf ...................... 128/287 |
| 3,665,922 A | 5/1972 | Skora ......................... 128/290 |
| 3,678,933 A | 7/1972 | Moore et al. ............... 128/296 |
| 3,683,921 A | 8/1972 | Brooks et al. .............. 128/296 |
| 3,694,867 A | 10/1972 | Stumpf ....................... 24/204 |
| 3,708,833 A | * 1/1973 | Ribich et al. ................. 24/450 |
| 3,708,837 A | 1/1973 | Chiba .......................... 24/204 |
| 3,726,752 A | * 4/1973 | Provost ....................... 24/444 |
| 3,768,479 A | 10/1973 | Widlund ..................... 128/287 |
| 3,849,840 A | * 11/1974 | Yamada et al. ............... 24/448 |
| 3,863,304 A | 2/1975 | Brumlik ..................... 24/204 |
| 3,867,935 A | 2/1975 | Eisdorfer et al. ........... 128/156 |
| 3,867,940 A | 2/1975 | Mesek et al. ............... 128/287 |
| 3,895,797 A | 7/1975 | Moore ..................... 273/32 A |
| 3,905,071 A | 9/1975 | Brumlik ..................... 24/204 |
| 3,949,128 A | 4/1976 | Ostermeier ................. 428/152 |
| 3,971,381 A | 7/1976 | Gibson ...................... 128/296 |
| 4,067,609 A | 1/1978 | Ness .......................... 297/220 |
| 4,082,886 A | 4/1978 | Butterworth et al. ........ 428/284 |
| 4,162,344 A | 7/1979 | Rones ........................ 428/212 |
| 4,169,303 A | * 10/1979 | Lemelson .................... 24/452 |
| 4,355,066 A | 10/1982 | Newman .................... 428/198 |
| 4,374,888 A | 2/1983 | Bornslaeger ................ 428/198 |
| 4,379,192 A | 4/1983 | Wahlquist et al. .......... 428/156 |
| 4,402,690 A | 9/1983 | Redfern ...................... 604/391 |
| 4,573,991 A | 3/1986 | Pieniak et al. .......... 604/385 A |
| 4,596,568 A | 6/1986 | Flug ........................... 604/369 |
| 4,600,618 A | 7/1986 | Raychok, Jr. et al. ........ 428/92 |
| 4,695,500 A | 9/1987 | Dyer et al. .................. 428/134 |
| 4,699,622 A | 10/1987 | Toussant et al. ............ 604/389 |
| 4,707,893 A | 11/1987 | Hashizume et al. .......... 24/446 |
| 4,725,473 A | 2/1988 | Van Gompel et al. ...... 428/156 |
| 4,737,404 A | 4/1988 | Jackson ...................... 428/284 |
| 4,739,635 A | 4/1988 | Conley et al. ................ 66/190 |
| 4,761,318 A | 8/1988 | Ott et al. ...................... 428/85 |
| 4,761,322 A | 8/1988 | Raley ......................... 428/198 |
| 4,776,068 A | * 10/1988 | Smirlock et al. ............. 24/306 |
| 4,834,738 A | 5/1989 | Kielpikowski et al. .. 604/385.2 |
| 4,883,707 A | 11/1989 | Newkirk .................... 428/219 |
| 4,894,060 A | 1/1990 | Nestegard ................... 604/391 |
| 4,936,840 A | 6/1990 | Proxmire ................. 604/385.2 |
| 4,959,265 A | 9/1990 | Wood et al. ................. 428/343 |
| 4,963,140 A | 10/1990 | Robertson et al. .......... 604/389 |
| 4,973,326 A | 11/1990 | Wood et al. ................. 604/391 |
| 4,984,339 A | * 1/1991 | Provost et al. ................ 24/452 |
| 5,032,122 A | 7/1991 | Noel et al. .................. 604/391 |
| 5,119,643 A | 6/1992 | Conley et al. ................ 66/190 |
| 5,158,819 A | 10/1992 | Goodman, Jr. et al. ..... 428/131 |
| 5,180,534 A | 1/1993 | Thomas et al. ............. 264/145 |
| 5,315,740 A | 5/1994 | Provost ....................... 24/452 |
| 5,326,612 A | 7/1994 | Goulait |

* cited by examiner

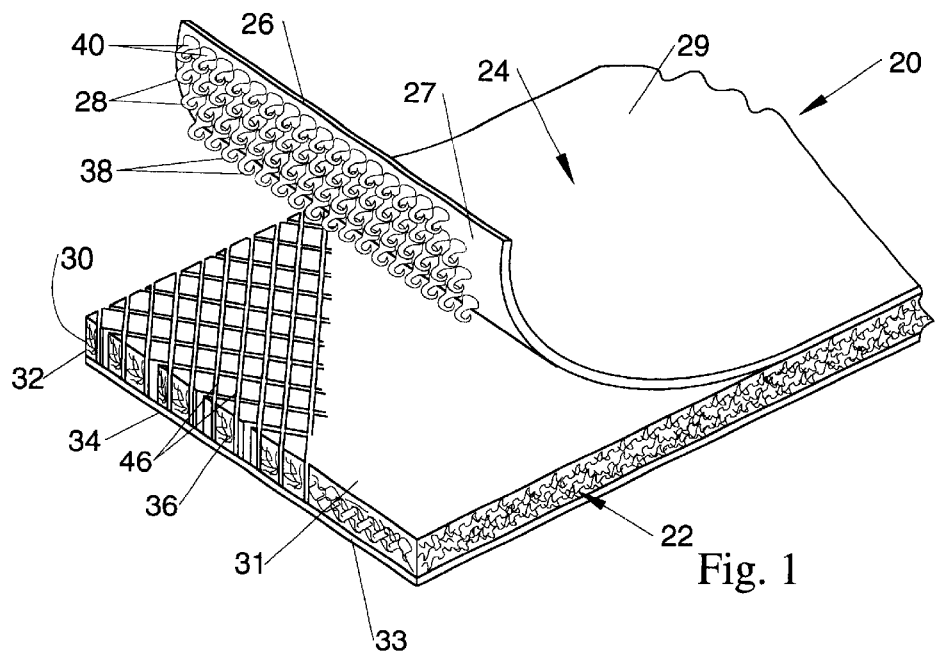
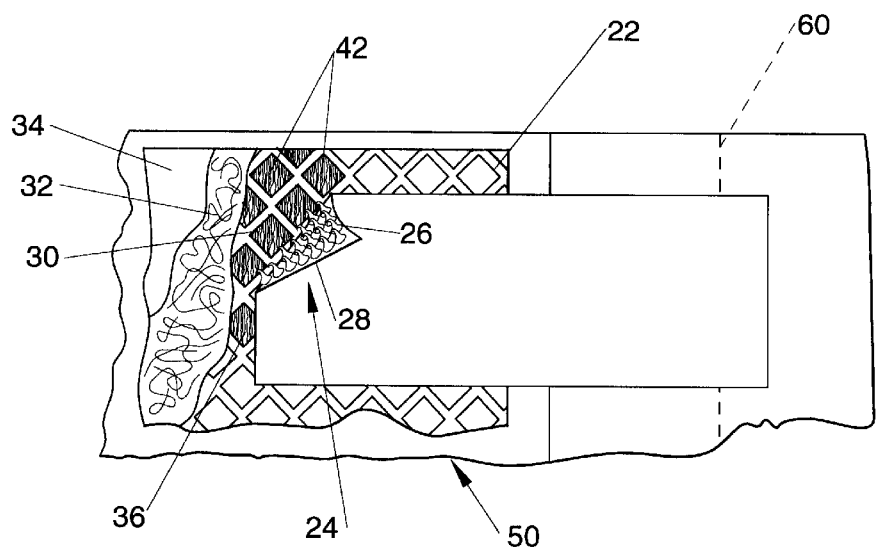
Fig. 2
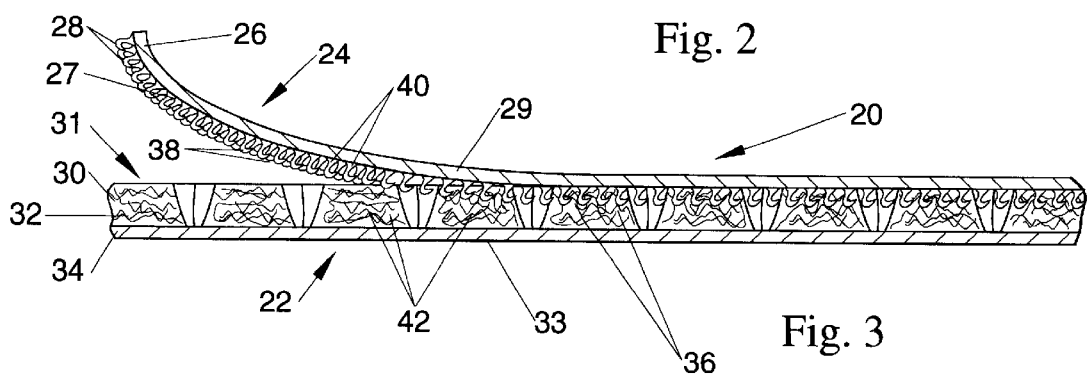
Fig. 3

MULTI-LAYER FEMALE COMPONENT FOR REFASTENABLE FASTENING DEVICE AND METHOD OF MAKING THE SAME

This application is a division of U.S. patent application Ser. No. 08/139,363 filed Oct. 19, 1993, which is pending, which is a division of U.S. patent application Ser. No. 07/703,426 filed May 20, 1991, which has been abandoned; and which is a continuation-in part of U.S. patent application Ser. No. 08/078,712 filed Jun. 17, 1993, which is pending, which is a division of U.S. patent application Ser. No. 07/668,817 filed Mar. 7, 1991, which has issued as U.S. Pat. No. 5,230,851, which is a continuation of U.S. patent application Ser. No. 07/305,354 filed Jan. 31, 1989, which has been abandoned.

FIELD OF THE INVENTION

The present invention relates to a female component for a mechanical refastenable fastening device. More particularly, this invention relates to a low-cost is multi-layer female component for such a fastening device, and a method for producing such a component.

BACKGROUND OF THE INVENTION

Refastenable fastening devices of the hook and loop-type are currently used widely in a great number of situations. Such refastenable fastening devices have been used in clothing, disposable articles, and various miscellaneous articles such as safety belts and the like. Such devices are used when it is desirable to create a refastenable bond between two or more articles or between several surfaces of the same article. In certain applications, these refastenable fastening devices have replaced conventional buckles, zippers, buttons, snaps, tie fasteners, and sewing.

A popular type of mechanical fastener currently in wide use which utilizes mechanical entanglement to create a refastenable bond is sold under the trademark "VELCRO". VELCRO fastening devices are described in greater detail in U.S. Pat. No. 2,717,437, U.S. Pat. No. 3,009,235, U.S. Pat. No. 3,266,113, U.S. Pat. No. 3,550,837, U.S. Pat. No. 4,169,303, and U.S. Pat. No. 4,984,339.

VELCRO fasteners utilize two components, a male component and a female component. The male and female components are often referred to as the hook and loop components, respectively. The hook component consists of a fabric which contains a plurality of resilient, upstanding hook-shaped elements. The female component of the fastening device consists of a fabric containing a plurality of upstanding loops on its surface. When the hook component and the loop component are pressed together in a face-to-face relationship to close the fastening device, the hooks entangle the loops forming a plurality of mechanical bonds between the individual hooks and loops. When these bonds have been created, the components will not generally disengage under normal conditions. This is because it is very difficult to separate the components by attempting to disengage all of the hooks at once. However, when a gradual peeling force is applied to the components, disengagement can be easily effected. Under a peeling force, since the hooks are comprised of a resilient material, they will readily open to release the loops.

This type of fastening device has been found especially useful on disposable articles such as disposable garments, disposable diapers, disposable packages, cartons and the like. Such fastening devices provide a secure closing means. However, the use of existing fastening devices of this type on disposable articles has been limited due to the fact that such fastening devices are relatively costly. The major reason that such fastening devices are costly is that they have high manufacturing costs. These high manufacturing costs are associated with both the hook and loop components of these devices.

Conventional hook and loop components are typically formed by making a fabric with a number of woven loops extending outwardly from a backing. The loops may be provided by weaving a base fabric containing supplementary threads to form the loops, or by knitting loops into a fabric. In other hook and loop components, the loops may be formed by pleating or corrugating processes. The hook components of such fastening devices are typically formed by subsequently cutting the loops. The cut loops serve as the hooks of the hook component.

These processes generally produce costly hook and loop fastening materials because they are relatively slow. The hook and loop components of such fastening devices are also usually made out of the same relatively expensive material. This material is generally relatively expensive for the hook component because the material used in the hook component needs to be resilient so that the hooks can disengage from the loop component when the device is opened. Conventional loop fastening materials are generally made entirely out of a single material. This material is generally relatively expensive due to the need of such material to be strong enough to hold the engaged hooks when subjected to forces applied on the fastening device.

Several attempts have been made to make alternative types of female components for fastening devices. However, such attempts have generally suffered from a number of drawbacks.

One such attempt is described in U.S. Pat. No. 3,708,833 issued to Ribich, et al. on Jan. 9, 1973. The Ribich, et al. patent discloses a refastenable fastening device having a female component that comprises reticulated urethane foam secured to a backing layer. The female component disclosed in the Ribich, et al. patent suffers from the drawback that foams typically do not have enough openings for the hooks of conventional hook components to penetrate. Reticulated foam does not have sufficient strength to hold such hooks when forces are applied to the fasting device. Further manufacturing reticulated foam is a relatively expensive process.

U.S. Pat. No. 3,905,071 issued to Brumilk on Sep. 16, 1975 discloses a "press-through self-gripping device." The device described in the Brumlik patent does not appear to be suitable for use in a refastenable fastening device that utilizes a conventional mating hook component with resilient hooks. The fastening device disclosed in the Brumlik patent is intended to be used for fastening one or more sheets of material between a gripping member and a receiving member. The gripping member disclosed in the Brumlik patent has rigid and stiff needle-shaped elements for gripping elements. These needle-like elements are particularly unsuitable for use in fastening devices on disposable absorbent articles. The disclosure of the Brumlik patent, thus, appears to be limited to devices that employ gripping elements adapted to penetrate and pass through several sheets of material and lodge inside a receiving member.

Therefore, there is a need for a low-cost fastening device for disposable articles. In particular, there is a need for such low-cost fastening devices to perform in a manner comparable to the more expensive commercially-available fastening devices.

It is an object of the present invention to provide an improved low-cost female component for a fastening device.

It is another object of the present invention to provide a female component for a fastening device that can be used with both commercially-available hook components having resilient individual hooks, as well as less expensive hook components with more brittle hooks than those currently in use.

It is a further object of the present invention to provide a low-cost female component that makes more efficient use of materials than existing fastening devices and that utilizes reduced amounts of expensive materials.

It is still another object of the present invention to form a low-cost female component for a refastenable fastening device by stacking materials on top of one another which have certain desired individual characteristics for entangling and engaging the hooks of a mating hook component.

It is a still further object of the present invention to provide a low-cost and improved method for producing such a female component.

These and other objects of the present invention will be more readily apparent when considered in reference to the following description and when taken in connection with the accompanying drawings.

SUMMARY OF THE INVENTION

The present invention provides a multi-layer (or multi-zone) female component or engaging a complementary hook component in a refastenable fastening device. The female component of the present invention is capable of engaging a hook component that has individual hook elements having blunt heads. The female component does not require individual loops of the conventional type to be present. Typically, the hooks will be engaged by elements that present the female component with a relatively flat outwardly-facing surface.

The female component comprises at least two, and preferably three layers or zones. Each zone has certain of the desired individual characteristics for entangling and holding the hooks of the mating hook component. The zones include a first zone (the "entanglement" zone), a second zone (the "spacing" zone), and a backing. The entanglement zone may be a woven fabric, a nonwoven web, or some other type of material that has fibers, strands, or the like to entangle the hooks of the hook component. There should be sufficient space between these fibers to admit the hooks of the hook component. The spacing zone may be any suitable material that provides space for the hooks to occupy after they have been admitted by the entanglement zone. The spacing zone may be comprised of the same type of material as the entanglement zone, or a completely different material. For instance, in one alternative embodiment, the spacing zone can comprise loose particles. The spacing zone will preferably be a "high loft" (high caliper) material so that it will be able to provide adequate space for the stems and heads of the hooks. The backing is adjacent to the spacing zone. The backing provides a foundation for the entanglement and spacing zones.

In one preferred embodiment, the entanglement zone comprises a first nonwoven web having a basis weight of between about 7 and about 15 g/yd$^2$ (about 8.5 to about 18 g/meter$^2$) and fibers with a denier of between about 2 and about 6; the spacing zone comprises a second nonwoven web having a basis weight of between about 7 and about 30 g/yd$^2$ (about 8.5 to about 36 g/meter$^2$) and fibers with a denier of between about 6 and about 15; and the entanglement and spacing zones are held in place relative to a film backing with the spacing zone in between the entanglement zone and the backing.

This arrangement of layers results in a lower cost female component. Less expensive materials can be used in the spacing zone, in lieu of using the same, relatively expensive raw material for the entire composition of the female component. The female component can also be produced by a lower cost laminating process, rather than the conventional weaving, knitting, pleating, or corrugating processes.

The preferred embodiment of the female component described above is formed by a method comprising the steps of:

(a) providing a first material having a basis weight of between about 7 and about 15 g/yd$^2$ (about 8.5 to about 18 g/meter$^2$) and being comprised of fibers with a denier of between about 2 and about 6 for a first zone;

(b) providing a second material having a basis weight of between about 7 and about 30 g/yd$^2$ (about 8.5 to about 36 g/meter$^2$) and being comprised of fibers with a denier of between about 6 and about 15 for a second zone;

(c) providing a backing material; and (d) securing at least the first material to the backing material so that the second material is positioned between the first material and the backing material.

The present invention also relates to a fastening device having a hook fastening component and a female component. The female component comprises the multi-layer female component of the present invention. The hook fastening component comprises a hook fastening component which had a base and a number of individual hooks extending from the base. The multi-layer female component and the complementary hook fastening component provide a secure refastenable closing means that will resist forces encountered during use.

The present invention also relates to disposable articles and more particularly to a disposable diaper having such an improved fastening device.

BRIEF DESCRIPTION OF THE DRAWINGS

While the specification concludes with claims particularly pointing out and distinctly claiming the subject matter which is regarded as forming the present invention, it is believed that the invention will be better understood from the following description in conjunction with the accompanying drawings in which:

FIG. 1 is a perspective view of the refastenable fastening device of the present invention.

FIG. 2 is a partially cut-away plan view of the multi-layer female component of the present invention shown in use with a tape fastening system of a disposable diaper (only a portion of which is shown).

FIG. 3 is a side view of the fastening device shown in FIG. 1.

DETAILED DESCRIPTION OF THE INVENTION

The Refastenable Fastening Device

Figure 3A:
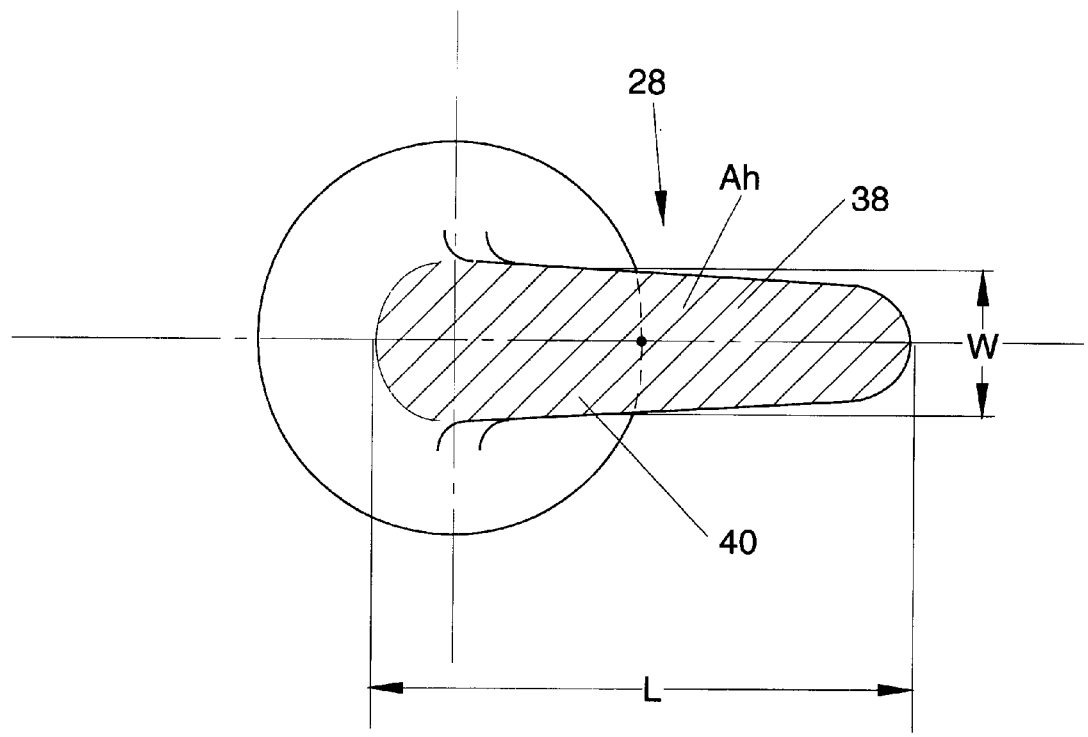
FIG. 3A is a plan view of an individual hook of the hook component.

1. Overall Characteristics of the Refastenable Fastening Device

A preferred embodiment of the refastenable fastening device of the present invention, fastening device 20, is shown in FIG. 1.

The fastening device 20 comprises the multi-layer female component 22 of the present invention and a complementary hook fastening component 24.

The male portion of the device, hook fastening component (or simply "hook component") 24, comprises a base, such as fabric 26 that has a first surface 27 and a second surface 29. The fabric 26 contains a plurality of upstanding engaging elements or "hooks" 28 extending from the first surface 27. The hooks 28 have heads 38. The heads 38 are on top of the shanks or stems 40 that extend from the first surface 27.

The female portion of the device, multi-layer female component (or simply "female component") 22, of the present invention receives and engages the hooks 28 of the hook component 24. The female component 22 shown in FIG. 1 has a first, outwardly-facing surface 31 and a second, inwardly-facing surface 33.

The female component 22 comprises three layers or zones: a first layer or zone, entanglement zone 30; a second layer or zone, spacing zone 32; and, a backing 34. The entanglement zone 30 contains a plurality of structural components or structural elements, such as fibrous elements (or simply "fibers") 36. The fibers 36 entangle the hooks 28 of the hook component 24. The spacing zone 32 spaces the entanglement zone 30 away from the backing 34. The backing 34 provides a foundation for the other zones.

The arrangement of the different zones of the female component 22 is shown in FIG. 1. The entanglement zone 30 is positioned on top of the spacing zone 32 and the backing 34. The entanglement zone 30 is the portion of the female component 22 that generally faces outward to form the first surface 31 of the female component 22. That is, the entanglement zone 30 is exposed so that it will be available to entangle the hooks 28 of the hook component 24. The spacing zone 32 is positioned between the entanglement zone 30 and the backing 34. The backing 34 is inwardly-oriented so it will be adjacent and generally joined to the portion of the article to which the female component 22 is attached.

The fastening device 20 of the present invention functions in the following manner. The fastening device 20 is closed when the female component 22 and the hook component 24 are pressed face-to-face against each other. When this happens, the hooks 28 are entangled by the structural elements of the female component 22 (or more specifically, by the fibers 36 of the entanglement zone 30). The spacing zone 32 provides space for the hooks, particularly, the heads 38 of the hooks 28 to occupy when the fastening device 20 is closed. The backing 34 provides a supporting foundation for the other zones or layers. With the hooks 28 mechanically entangled by or "hooked" onto the fibers 36 (shown in the portion of the fastening device 20 to the right side in FIG. 1), the connection between the male and female components resists the forces that may be exerted on the fastening device 20.

The fastening device 20 is opened by peeling the hook component 24 away from the female component 22 (or by peeling the female component 22 away from the hook component 24). If the hook component 24 has resilient hooks, the peeling action may cause the hooks 28 to be bent so that they are disengaged from mechanical entanglement with the fibers 36 of the entanglement zone 30. In other cases (particularly if the hooks 28 are relatively inflexible), the hooks 28 may disengage by breaking the fibers of the female component 22. In either case, the hooks 28 are disengaged, and the hook component 24 is completely detached from the female component 22. The fastening device is then capable of being refastened in the manner described above.

The components of the refastenable fastening device 20 are discussed more fully in the following sections of this description. The multi-layer female component 22 of the present invention is discussed in Section 2 below. The hook component 24 is discussed in Section 3. Section 4 gives examples of uses of the refastenable fastening device 20.

2. The Multi-Layer Female Component

The multi-layer female component 22 shown in FIGS. 1–3 is one preferred embodiment of the female component of the refastenable fastening device 20 of the present invention.

Several alternative embodiments are shown in the figures that follow FIGS. 1–3. It should be understood that the zones of the female component 22 are generally shown in schematic form in most of the figures, for simplicity. The configuration of the zones and the bonding between the zones of the female component 22 more closely resembles that shown in FIG. 4C in the actual product.

The definitions of several terms are first provided to assist the reader in understanding the present invention.

The term "multi-layer" is intended to include structures that are comprised of subcomponents arranged in multiple zones, as well as those arranged in multiple layers. (Preferably, these multiple zones are generally parallel zones.) The term "multi-layer", as used herein, thus, may be synonymous with the term "multi-zone". The term "layer" may be synonymous with the term "zone".

Therefore, a female component that comprises a zone of loose material sandwiched between two layers would be considered to be a "multi-layer" female component. Other arrangements of zones and layers are also within the scope of the present invention. The "layers" referred to herein, thus, may actually comprise strips of material, loose or bonded particles or fibers, laminates of material, or other combinations of such materials, such as several sheets or webs of the types of material described below. Thus, the term "multi-layer" is not limited to structures having components that are in the form of layers or sheets of material.

The term "generally parallel" is used above to describe the arrangement of the zones of the female component 22. The term "generally parallel", as used in this context, is intended to include not only arrangements of layers or zones which are flat and parallel, but also arrangements that were originally generally flat and parallel prior to bonding, and after bonding are in the form of the arrangement shown in FIG. 4C.

The term "loop component", as used herein, refers to the portion of a hook and loop-type fastening device that is designed to engage the hooks of a complementary hook component. The multi-layer female component 22 of the present invention could be thought of as a replacement for a loop component. Generally, however, the multi-layer female component 22 does not require that loops of material be specifically formed to engage the hooks of a mating hook component. Typically, the individual structural elements 36 (e.g., the fibers of the woven or nonwoven material) that form the entanglement zone 30 will serve to entangle the hooks 28, even though these structural elements are not necessarily "looped".

The multi-layer female component 22 does not require the formation of loops of material that extend outward from a backing. (Thus, for the purposes of the present invention, the female component 22 may be considered to be "loop-less".)

The term "loop", as used herein, refers to a fibrous material that is curved or doubled to form a closed curve into which a hook may be inserted. The term "loop", as used herein, also includes materials made by any process in which fibrous materials are manipulated, individually or collectively, to form loops, regardless of whether the fibers are formed into a closed or partially open curve. The term "loop", as used herein, however, does not include the fibrous elements disposed within a web or fabric which are not separately manipulated.

The multi-layer female component 22 of the present invention should have certain characteristics.

The multi-layer female component 22 operates upon the principle that engaging the hooks of a hook component involves several separate functions. These include the functions of entangling the hooks and providing space to "store" the hooks after they have been entangled. The multi-layer female component 22 comprises zones that each have characteristics specifically suited for serving at least one of the functions of receiving, entangling, and holding the hooks of the mating hook component.

Figure 3B:
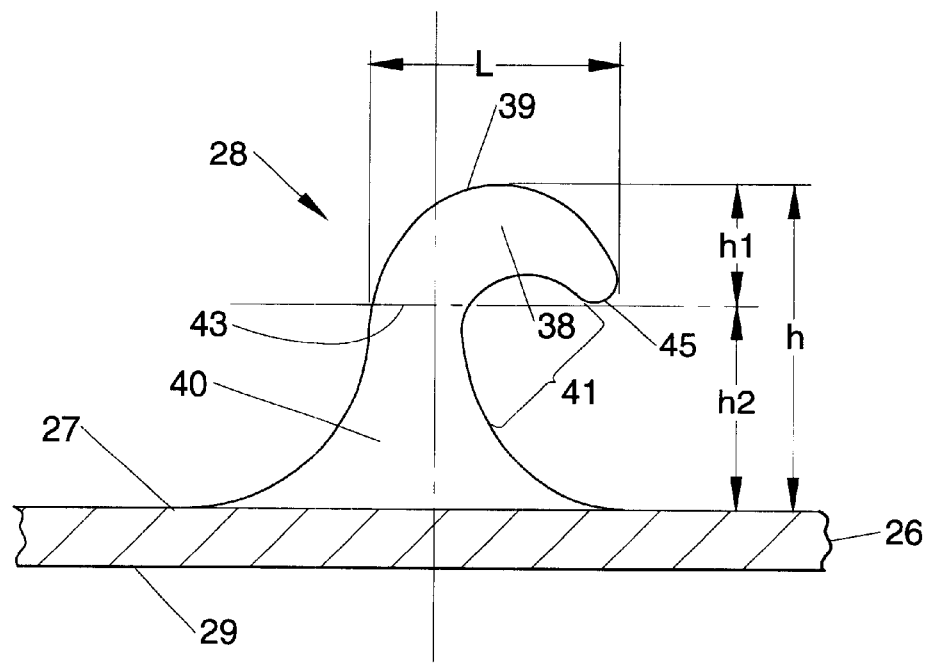
FIG. 3B is a side view of the hook shown in FIG. 3A.
Figure 4A:
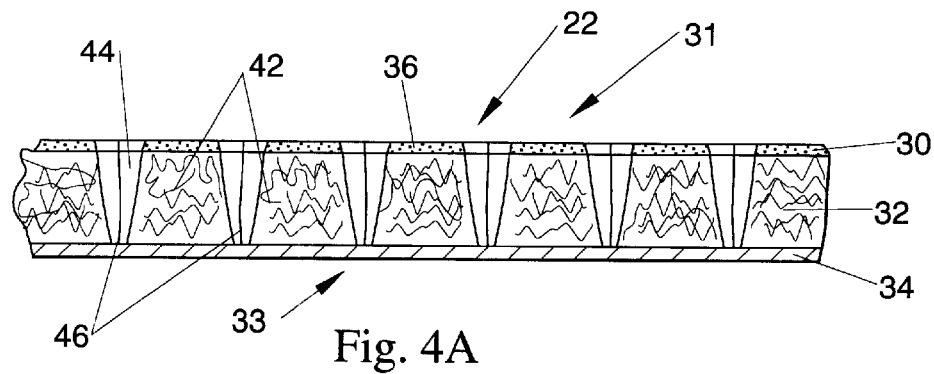
FIGS. 4A and 4B are a side view and a partially cut-away plan view of an alternative embodiment of the female component of the present invention in which the diameter of the fibers are the same denier in the entanglement and spacing zones.

The individual fibers of the material that form the layers generally provide the female component 22 with an outwardly-facing surface 31 that is relatively level, planar, or flat in comparison to the surfaces of conventional loop components which have many loops of material extending outward from a backing. The term "planar", as used herein, includes, but is not limited to those surfaces that lie in a single, relatively flat plane as shown in FIGS. 1–3, as well as those surfaces that are gradually curved such as shown in FIG. 4C.

The multi-layer female component 22 should have sufficient open space between the structural elements that comprise both its entanglement zone 30 and its spacing zone 32. The term "structural elements", as used herein, refers to the individual fibers, yarns, strands, loose particles, and the like which may comprise the webs, fabrics, screens, and the like that form these respective zones. Alternatively, or additionally, these structural elements should be able to spread, or otherwise move to create the open space needed to accommodate the hooks 28 of the mating hook component 24.

The materials that comprise the zones of the female component 22 may be described as "being capable" of providing a certain amount of open space between their structural elements. This terminology is intended to include materials that originally have the specified open space, those that have structural elements that move to provide such open space, and those materials provide such open space in both of these manners. The movement of the structural elements to provide open space is particularly apparent in the case of the spacing zone 32.

For example, the spacing zone 32 may be comprised of loose particles that are initially in contact with each other. As a result, there may be some portions of the spacing zone 32 that have essentially no open space between the particles. These loose particles should be able to spread apart, be pushed downward (toward the backing 34 or the substrate), or otherwise move out of the way to make the open space needed to accommodate the hooks 28 of the mating hook component 24. The open space between the structural elements of the female component 22 described herein, thus, means that the female component has or is capable of providing a multiplicity of openings between its structural elements.

The female component 22 should allow the hooks 28 of the mating hook component 24 to readily enter between the openings (the spaces, or interstices) between the fibers or other structural elements that comprise the entanglement and spacing zones 30 and 32. The hooks 28 should be able to enter without piercing through these fibers or other structural elements. The hooks 28 should be able to enter, and if necessary, spread these fibers or other structural elements apart. This should, however, require the application of relatively little, if any force (e.g., in comparison to that needed when using a "press-through" device such as that described in the Brumlik patent discussed above).

When the female component 22 is provided with such space between its structural elements, it will work with conventional, commercially available hook materials. The female component 22, however, is not limited to use with conventional hook materials having flexible, resilient hooks. It can also be used with hook materials that have less expensive, more brittle hooks. The female component 22 is also particularly well-suited for use with hook components having hooks with generally rounded and/or blunt heads. It does not require specially-made rigid, sharp hooks to be used. It is, however, possible for sharp hooks to be used with the female component 22.

Thus, when the female component 22 of the present invention is said to be "capable" of engaging a hook component with a certain type of hooks, this means that the type of hook component referred to can be used. The female component 22, however, is typically not limited to use with such a hook component; other types of hook components can usually also be used with the female component.

The amount of open space required between the structural elements of the entanglement and spacing zones 30 and 32 depends on the size of the hooks 28 of the hook component 24. The dimensions of various parts of a hook 28 of one type are shown in FIGS. 3A and 3B. The hook 28 shown in FIGS. 3A and B has an overall height h, and a head 38 with a certain length, width, and height, designated l, w, and h1, respectively.

The "head" of the hooks, as that term is used herein, refers the portions of the hook 28 that project laterally (or radially) outward from the stems 40 in one or more directions. Often, there will not be a line of demarcation between where the stem 40 of the hook 28 ends and where the head 38 begins. For the purposes of the present invention, the head 38 of the hooks 28 will be considered to begin at the portion of the stem 40 designated 43 in FIG. 3B. This is the portion of the stem 40 that is spaced the same perpendicular distance away from the backing 36 as the lowermost point 45 on the head 38 of the hook 28. The lowermost point 45 is the portion of the head 38 spaced the smallest perpendicular distance from the base 26 of the hook component 24.

The length l and width w of the hook's head 38 are most important in determining the amount of open space required between the structural elements of the entanglement and spacing zones 30 and 32. More specifically, the amount of open space required between the structural elements is generally determined by the dimensions known as the projected plan view area (the "projected plan view dimensions") of the heads 38 of the hooks 28. This area is represented by reference letter $A_h$ in FIG. 3A. This is the surface of the hooks 28 that will initially come in contact with the female component 22 of the present invention. Thus, the open space provided by between the structural elements of the entanglement and spacing zones 30 and 32 should be either slightly larger in dimensions than the projected plan view dimensions of the heads 38 of the hooks 28, or the structural elements should readily spread apart to such dimensions. Therefore, when large hooks 28 are used (that is, hooks having a relatively large $A_h$), there should be more open space than if relatively small hooks 28 are used.

There are several factors that determine the amount of open space between the structural elements of the multi-layer female component.

One factor is the type of structure used in the entanglement and spacing zones 30 and 32. The amount of open space in the entanglement and spacing zones 30 and 32 will differ depending upon whether these zones comprise woven, nonwoven, or some other type of material.

If, for instance, the entanglement and spacing zones 30 and 32 both comprise nonwoven webs, the fibers that comprise such nonwoven webs will spread easier without the application of force to accommodate the hooks 28 than will the yarns of a woven fabric (or the strands of a screen, or the like). That is because in a woven fabric, each point where one yarn crosses over another yarn will tend to be fairly rigid in the presence of forces that attempt to spread the fabric apart. Because of this resistance to spreading, it is generally preferable the dimensions between adjacent yarns in a woven fabric (i.e., the size of the interstices) be at least slightly larger than the projected plan view dimensions of the heads of the hooks. The same is true of the dimensions between the strands of a screen, and the like.

The amount of bonding between the structural elements in each layer or zone will also determine the open space in the entanglement and spacing zones 30 and 32. The same is true of the bonding between the different zones of the female component. The bond sites created by the bonds between the structural elements within each layer or zone tend to reduce the spreading of structural elements needed to accommodate hooks 28. The bond sites also tend to interfere with the penetration is of the hooks 28 of the mating hook component 24. The same is true for the bonds between the different layers or zones of the female component 22.

The basic elements of the multi-layer female component 22 of the present invention are from top to bottom: a first zone, entanglement zone 30; a second zone, spacing zone 32; and a backing 34.

The entanglement zone 30 permits the hooks of a mating hook component to penetrate through its thickness. The entanglement zone 30 entangles the hooks until it is desired to open the fastening device 20. The entanglement zone 30 may be referred to by any suitable name that describes its function, such as the "penetrable/entanglement layer" or simply as the "entanglement layer" 30. The entanglement zone 30 should have certain characteristics.

The entanglement zone 30 should have sufficient open area so a plurality of the hooks of a mating hook component may penetrate its thickness when a hook component is placed in a face-to-face relationship with the female component 22. It is not necessary, however, that all of the hooks of the hook component penetrate the entanglement zone 30. It is only necessary that a sufficient number of hooks penetrate the entanglement zone 30 for the female component 22 to be operable. The openings in the entanglement zone 30 should be sufficiently large relative to the size of the hooks so that the hooks which penetrate the entanglement zone 30 are able to do so without forcibly piercing the material of the entanglement zone 30. Further, the total number and distribution of such open spaces per unit area of the female component 22 should be adequate to accommodate a sufficient number of hooks 28 of the mating hook component 24.

The entanglement zone 30 should also be able to entangle and hold a sufficient number of the hooks of the mating hook component 24 for the fastening device 20 to be operable. Therefore, the number of fibers or other structural elements that comprise the entanglement zone 30 must be sufficient to entangle and hold the hooks 28 until a peeling force is applied to open the fastening device 20. These structural elements must also have sufficient strength to hold the hooks when forces that are not intended to open the fastening device 20 are applied. In addition, in some embodiments, it is preferred that the structural elements comprising the entanglement zone 30 have the ability to withstand repeated disengagement of the hooks without being destroyed or disrupted by the removal of the hooks.

The caliper of the entanglement zone 30 should be sufficient that an adequate number of the heads 38 of the hooks 28 are able to catch onto the structural elements of the female component 22. The caliper can be very small if, at a low caliper, the entanglement zone 30 contains a sufficient number of structural elements which are strong enough to hold the hooks 28 of the mating hook component 24. The caliper of the entanglement zone 30 can range to as large as the total height h of the hooks, or more. However, embodiments in which the caliper of the entanglement zone 30 is larger than the height of the hooks are generally less preferred because they do not take advantage of the spacing zone. (When the caliper of the entanglement zone 30 is larger than the height of the hooks, the hooks will not be long enough to reach and utilize the spacing zone). Therefore, preferably, the caliper of the entanglement zone 30 is generally less than the height h of the hooks, so the spacing zone 32 also provides a benefit.

The material used in the entanglement zone 30 should, preferably, be relatively soft if the female component 22 is used in a fastening system on a disposable absorbent article, so that the female component 22 will be comfortable for the wearer in the event it contacts the wearer's skin.

Figure 5:
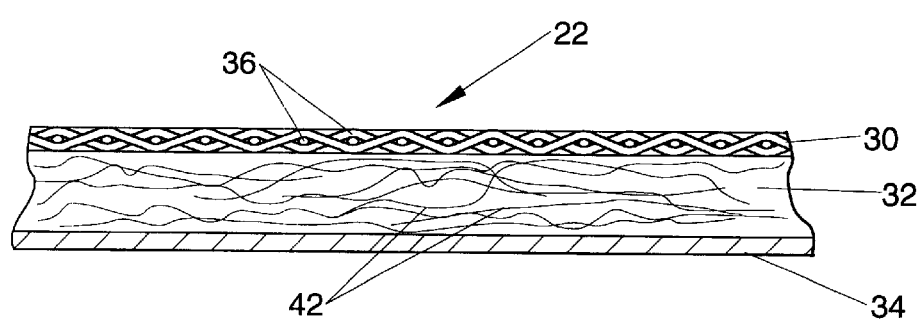
FIG. 5 is a simplified side view of an alternative embodiment of the multi-layer female component of the present invention in which the entanglement zone is a woven fabric.

The entanglement zone 30 may be in any suitable structural form. For instance, in the preferred embodiment shown in FIGS. 1–3 of the drawings, the entanglement zone 30 is a nonwoven layer or web of material. The term "nonwoven", as used herein, refers to fabrics made of fibers held together by interlocking or bonding which are not woven, knitted, felted, or the like. (The term "fabric", as used herein, may refer to a nonwoven web, a woven material, or other types of fabrics.) Alternatively, as shown in FIG. 5, the entanglement zone 30 may be a woven fabric. In still other alternative embodiments, the entanglement zone 30 could comprise netting, perforated film, foams, or any other type of material that is capable of providing open spaces for hooks to penetrate and entangling those hooks until it is desired to open the fastening device 20.

If a nonwoven web is used as the entanglement zone 30, the characteristics used in the nonwoven fabric industry, such as basis weight, length and denier of fibers are used to specify those nonwoven materials which have the qualities set forth above. The open area between structural elements and the number of the structural elements (at least on a relative basis), can be approximated from the basis weight of the web. (For instance, a nonwoven web of a lesser basis weight will generally have greater open area and fewer structural elements than a web of greater basis weight having the same denier and length fibers.) The strength of the web for use in a female component (at least on a relative basis) can be approximated from the basis weight of the web and the denier and material composition of the fibers.

Suitable nonwoven webs include those having a basis weight of between about 7 and about 35 g/yd$^2$ (about 8.5 to about 42 g/meter$^2$), more preferably, between about 7 and about 30 g/yd$^2$ (about 8.5 to about 36 g/meter$^2$), and most preferably, between about 7 and about 15 g/yd$^2$ (about 8.5 to about 18 g/meter$^2$). The basis weight is measured by diecutting a certain size sample and weighing the sample on a standard scale. The weight and area of the sample determines the basis weight of the sample. The density can be calculated from the basis weight of the sample and its caliper.

The lengths of the fibers that comprise such nonwoven webs may depend upon the type of process used to make the nonwoven web. For instance, if a carded nonwoven web is used, the fibers that comprise such a web can have lengths that can range from about 0.5 inch to about 5 inches (from about 1 cm. to about 13 cm.). Preferably, the fibers are between about 2 inches and about 3 inches (between about 5 cm. and about 8 cm.) long. If, on the other hand, a spunbonded nonwoven web is used, the fibers or filaments of such a web will typically be continuous length.

The diameter of the fibers is one factor that determines the strength of the nonwoven web. Generally, the larger the diameter of the fiber is, the stronger the fiber. The maximum diameter that can be used depends in part on the size of the gap 41 defined by the hooks 28. The term "gap", as used herein, refers to the openings formed by the heads 38 of the hooks. These are the portions that grab the fibers or other structural elements. The diameter of the fibers 36 must not be so great that the heads 38 of the hooks 28 are unable to fit around and entangle the fibers 36. Typically, for currently available hook components, the fibers 36 should have a denier of between about 2 and about 15, more preferably, between about 2 and about 6. If hook components become available that have hooks 28 which are substantially smaller than those currently available, the denier of the fibers could be between about 0.5 and about 15, or less. It is possible that fibers having deniers as low as between about 0.5 and about 1.0, or less, could be used. Such fibers may be referred to as "micro denier" fibers. (Denier is a unit of fineness of a yarn weighing one gram for each 9,000 meters, thus a 100 denier yarn is finer than a 150 denier yarn.)

The fibers of such nonwoven webs can be comprised of any suitable material, including, but not limited to polyesters (such as polyethylene therapthalate (or PET)), polyethylene, and polypropylene, or any combinations of these and other suitable materials known in the nonwoven fabric industry. For example, a suitable nonwoven web could comprise a mixture of fibers of two different types of materials (e.g., a mixture of polyester and polypropylene fibers). In still other cases, a suitable nonwoven web could be comprised of fibers that are comprised of more than one material (e.g., a polyester fiber coated with polypropylene). Suitable polypropylene fibers for such a nonwoven web include those available from the Hercules, Inc. of Wilmington, Del. as product numbers T-181, T-182, and T-196.

The nonwoven webs suitable for use in the entanglement zone 30 can be produced by many different processes. For example, the nonwoven web could be either a carded or a spunbonded web. Such nonwoven webs can be made by any suitable commercial carding or spunbonding processes.

Suitable materials for such an entanglement zone 30 can be obtained in the form of a carded nonwoven web from Veratech Nonwoven Group of the International Paper Company of Walpole, Mass. 02081 by specifying the desired characteristics described herein (such as basis weight, fiber denier and composition). Suitable spunbonded nonwoven webs can be obtained from the Nonwovens Division of the James River Corporation located in Simpsonville, S.C. (It is expressly not admitted, however, that any of the materials described herein are known to have been used in fastening devices.)

Another example of a suitable carded nonwoven web can include materials that have been used as topsheets in diapers and other disposable absorbent articles (that is, provided they have the characteristics described herein).

The orientation of the structural elements 36 in the entanglement zone 30 is important. This is particularly true when a nonwoven web is used for the entanglement zone 30. The orientation of the fibers 36 in such a preferred entanglement zone 30 is preferably primarily in a single direction.

In addition, as shown in FIG. 2, when the female component 22 is incorporated into a refastenable fastening device 20 on a disposable diaper 50 (a portion of which is shown), the orientation of the structural elements 36 in the entanglement zone 30 relative to the edges of the diaper 50 is also important. The structural elements 36 of the entanglement zone 30 are preferably oriented so that they generally parallel to the longitudinal edges 60 of the diaper 50.

Such an orientation of the structural elements 36 in the entanglement zone 30 provides the greatest resistance to the disengagement of the hooks 28 when the fastening device 20 is subjected to the forces typically exerted on a diaper fastening system. These forces are usually applied in the plane of the interface between the fastening components in a direction parallel to the end edges of the diaper. The orientation of structural elements 36 referred to above can be contrasted with the situation in which the structural elements are perpendicular to the longitudinal edges 60 of the diaper 50. In this latter less desirable case, the structural elements 36 would run in the same direction as (or parallel to the direction of) such forces. In the latter case, the structural elements 36 may not be as able to serve as a "catch" for the hooks 28 of the mating hook component.

A woven fabric could be used in the entanglement zone 30. The woven fabrics used in the entanglement zone 30 should have an open weave. Typically, such fabrics will have a geometric weave. Suitable woven fabrics may have weaves with square, rectangular, or other shape openings. The spacing between adjacent yarns in the direction of the plane of the fabric should, preferably, be at least slightly larger than the projected plan view dimensions of the heads 38 of the hooks 28 of the mating hook component 24.

In those cases where the heads 38 of the hooks have length and width dimensions that are not equal (for example, where the hooks 28 have heads 38 which define a rectangular projected plan view area $A_h$), the openings in the woven fabrics can be made of a corresponding slightly larger size and dimensions than the heads 38 of the hooks 28. In such cases, the openings in the woven fabric should be oriented to register with the heads 38 of the hooks 28 when the hook component 24 is brought into contact with the female component 22. In alternative embodiments, the spacing between adjacent yarns could be at least as great as the largest of the plan view dimensions of the heads 38 of the hooks 28 so it will not matter which way the fabric is oriented when the hook component 24 is brought into contact with the female component 22.

Suitable woven materials can handle hooks 28 of the dimensions specified in Section 3 below. Thus, the woven materials used in the female component 22 may have openings that include, but are not limited to, the shape of rectangles that are in the following sizes: slightly greater than about 1 mm. by about 0.2 mm; slightly greater than about 0.5 mm by about 0.2 mm.; slightly greater than about 0.25 mm. by about 0.1 mm; or any combination of these length and width dimensions. In addition, with different size and shapes of hooks 28, the openings could be larger or smaller, or of different shapes. Examples of a commercially-available woven material suitable for use as the entanglement zone 30 are knits like women's Nylons.

The yarns that comprise these woven fabrics can be made of any suitable natural materials, such as cotton or wool, etc., or synthetic materials such as Nylon, rayon, and polyester, to name few. Similar materials can be used for entanglement zones 30 that are arranged in other structural forms. Thus, the yarns, strands, and the like that comprise the structural elements of screens, netting, and the other types of entanglement zones may also be comprised of the foregoing materials.

In other alternative embodiments, the entanglement zone 30 may comprise a perforated film. Suitable perforated films may be in the nature of, and manufactured in accordance with the processes described in the following patents: U.S. Pat. No. 3,929,135 entitled "Absorptive Structure Having Tapered Capillaries", issued Dec. 30, 1975 to Thompson; U.S. Pat. No. 4,324,246 entitled "Disposable Absorbent Article Having a Stain Resistant Topsheet", issued Apr. 13, 1982 to Mullane, et al.; U.S. Pat. No. 4,342,314 entitled "Resilient Plastic Web Exhibiting Fiber-Like Properties", issued Aug. 3, 1982 to Radel, et al.; and U.S. Pat. No. 4,463,045 entitled "Macroscopically Expanded Three-Dimensional Plastic Web Exhibiting Non-Glossy Visible Surface and Cloth-Like Tactile Impression", issued Jul. 31, 1984 to Ahr, et al. The disclosures of all these patents are hereby incorporated by reference herein.

The spacing zone 32 lies under the entanglement zone 30. The spacing zone 32 operates in the following manner. When the fastening device 20 is closed, the hooks 28 of the mating hook component 24 first pass through the entanglement zone 30 into the spacing zone 32. The hooks 28 may initially penetrate the spacing zone 32 to a greater depth than they will eventually be located in when they have engaged the structural elements 36 of the entanglement zone 30. In other words, there is usually an inward, then outward movement of the hooks 28 before they hook onto the structural elements 36 of the entanglement zone 30.

The spacing zone 32 must, therefore, provide space for the hooks 28 of the mating hook component 24 to penetrate before they hook onto the fibers 36 of the entanglement zone 30. The spacing zone 32 must also provide space for the hooks 28 to occupy after the hooks 28 come to rest in the spacing zone 32. The spacing zone 32, like the entanglement zone 30, should be some type of structure that has sufficient space between its structural elements to readily admit the hooks 28 of the mating hook component 24. Alternatively, or additionally, the structural elements of the spacing zone 32 should be arranged into a structure that is flexible enough for the structural elements to move out of the way of the hooks 28 of the mating hook component 24 when a hook component 24 is placed in a face-to-face relationship with the female component 22.

The spacing zone 32 can be any type of structure having the above open space characteristics that separates the entanglement zone 30 from the backing 34, or if there is no backing 34, from the substrate. The spacing zone 32 can, thus, be a layer or web of material. Alternatively, the spacing zone 32 can be some type of structure which simply separates the entanglement zone 30 from the backing 34 and occupies space. Examples include beads, and other types of loose material. The spacing zone 32, thus, does not have to be comprised of a material having the strength needed to make it capable of engaging and holding the hooks. It is, however, within the scope of the present invention for the spacing zone 32 to be comprised of a material capable of engaging and holding the hooks 28 of the hook component 24.

The spacing zone 32 is also, preferably resilient. A resilient spacing zone 32 is especially desirable when the fastening device is used on disposable absorbent articles. This allows the spacing zone 32 to continue to maintain space between the entanglement zone 30 and the backing 34, even after the female component 22 has been compressed during manufacturing, packaging, in use, and the like.

The spacing zone 32 is typically thicker (that is, it has a greater caliper or is more "lofted") than either the entanglement zone 30 or the backing 34. The greater caliper is needed because the spacing zone 32 must provide sufficient space to store the heads, and in many cases, at least a portion of the stems 40 of the hooks. The spacing zone 32 may, therefore, be referred to as a "high loft" material.

The caliper of the spacing zone 32 required depends on the height of the hooks 28 of the mating hook component 24. More particularly, the caliper depends on the dimension designated $h_1$ in FIG. 3B, which represents the height of the heads 38 of the hooks 28. The caliper of the spacing zone 32 should be at least as large as the height $h_1$ of the heads 38 of the hooks 28. This will assure that there is room to accommodate the inward and outward movement needed for the hooks 28 to hook onto the structural elements 36 of the entanglement zone 30.

The caliper of the spacing zone 32 can range to as large as the total height of the hooks h, or more. Thus, there is no fixed upper limit on the caliper of the spacing zone 32. In some embodiments, the caliper of the spacing zone 32 may be set so that the total caliper of the entanglement zone 30 and the spacing zone 32 is about the same as the height h of the hooks 28 to assure a good fit between the female component 22 and the hooks 28 of the mating hook component 24. The caliper of the spacing zone 32 should, however, preferably only be slightly larger than the height h1 of the heads 38 of the hooks 28 of the mating hook component 24. If the caliper of the spacing zone 32 is any greater, the additional material used to create such additional caliper will not be used, and will in effect, be wasted.

The caliper of the spacing zone 32 may more specifically, by way of example, be sufficient to accommodate hooks of the sizes that are discussed in greater detail in Section 3 below. For instance, if the hooks 28 are between about 0.015 inch and about 0.025 inch (about 0.38 mm. to about 0.64 mm.) in overall height and have heads 38 which are about 0.3 mm. in height, the caliper of the spacing zone 32 should generally range from between slightly greater than about 0.3 mm. to about 0.38 mm, or to about 0.64 mm, respectively. (All caliper dimensions can also be measured in combination with the caliper of the entanglement zone 30). In still other embodiments, the caliper of the spacing zone 32 can be more or less depending on the size of the hooks 28 of the mating hook component 24. For example, the caliper of the spacing zone 32 can be as small as about ½ or ¼ of the calipers set forth above, or less, if proportionately smaller hooks 28 are used.

The spacing zone 32 can be in many different structural forms. The spacing zone 32 can comprise nonwoven webs, woven fabrics, netting, loose filler material such as beads, pellets, packing filler, or bubbled film (this will work if the bubbles are sufficiently small that the hooks can go into the space between the bubbles), perforated film, foams, pieces of sponge, and any other type of material that is capable of providing space for hooks to penetrate at least partially into the thickness of the same and spacing the entanglement zone 30 away from the backing 34.

Suitable nonwoven webs for use in the spacing zone 32 may either be identical to those used for the entanglement zone 30, or of different properties and characteristics. Such webs may be made by any of the processes specified above for making the entanglement zone 30. In addition, melt blown nonwoven webs may also be suitable for use in the spacing zone 32.

Suitable nonwoven webs include those having a basis weight of between about 7 and about 35 g/yd$^2$ (about 8.5 to about 42 g/meter$^2$), more preferably, between about 7 and about 30 g/yd$^2$ (about 8.5 to about 36 g/meter$^2$), and most preferably, between about 10 and about 30 g/yd$^2$ (about 12 to about 36 g/meter$^2$).

The nonwoven webs used in the spacing zone 32 should be comprised of fibers that have a denier of between about 2 and about 15, more preferably, between about 6 and about 15. Most preferably, the denier of the fibers in the spacing zone 32 is about 9. Thus, the structural elements, such as fibers 42, preferred for use in the spacing zone 32 are preferably thicker than those in the entanglement zone 30. Thicker fibers are more desirable because when the fibers are stacked (as described below), it is possible to create a spacing zone 32 having a relatively large caliper with fewer fibers. Further, using thicker fibers for the spacing zone 32 does not result in any discomfort to the wearer, because the finer, softer fibers of the entanglement zone 30 will typically cover the spacing zone 32.

Preferably, if the spacing zone 32 comprises a nonwoven material, the fibers 42 of such a material are randomly-oriented. A random orientation will cause the fibers 42 in the spacing zone 32 to "criss-cross" and stack upon one another to create loft (or height). This will provide additional space for the hooks 28 of the mating hook component 24 to occupy when the hook component 24 engages the multi-layer female component 22.

The orientation of fibers in the various zones can be analogized to an arrangement of logs. If several logs are laid side-by-side, the height of the group of logs will be only equal to the diameter of the logs. However, if the logs are oriented in different directions, e.g., if they are stacked (for instance, as in a log cabin), the height of the stack would be equal to the sum of the diameters of the stacked logs.

The fibers in the spacing zone 32 may preferably also be crimped for additional loft. The term "crimped", as used herein, means that the fibers are wavy or bent along their lengths. The fibers may be crimped (preferably before carding, or the like) by any suitable commercial crimping process. The fibers 42 in such a nonwoven spacing zone 32 preferably have at least about 10 crimps/inch (about 4 crimps/cm.), and more preferably at least about 14 crimps/inch (an average of about 5.5 crimps/cm.).

Suitable commercially-available nonwoven materials for such a spacing zone 32 having the above characteristics can be obtained from Veratech Nonwoven Group of the International Paper Company of Walpole, Mass.

Suitable woven fabrics for use in the spacing zone 32 may either be identical to those used in the entanglement zone 30, or may be woven fabrics with different properties and characteristics.

Suitable loose materials for use in the spacing zone 32 can be any of those types of loose materials specified above. The loose materials can be particles of any shape. The loose materials can be cubic, polyhedral, spherical, rounded, angular, or irregularly shaped. The particles of loose material can be of uniform size or randomly sized. The size of each particle of such loose material can range from equal to or slightly less than the caliper of the spacing zone 32 to many times less than the caliper of the spacing zone 32.

Suitable perforated films for use in the spacing zone 32 may either be identical to those used in the entanglement zone 30, or may have different properties and characteristics.

The backing 34 is positioned beneath both the entanglement zone 30 and the spacing zone 32. The backing 34 provides a foundation for these other two zones. The backing 34 serves as a surface to which the other zones can be affixed. The backing 34 is optional, however. In an alternative embodiment in which there is no backing, the entanglement zone 30 and the spacing zone 32 can be bonded directly to the substrate (the surface of the article to which the female component is to be attached), and the substrate will serve the function of the backing.

Many types of material are suitable for use as the backing 34. The backing 34 preferably should be some type of material that the hooks 28 of the mating hook component 24 will not penetrate. (Although the backing 34 is not limited to such a material.) The backing 34 could be a film, a nonwoven web, a woven fabric, or any other suitable type of material. The backing 34 is generally a layer of material. The backing 34 can be made of polyester, polyethylene, or polypropylene, or any other suitable material. Suitable materials for use as the backing 34 include any commercially-available low gauge (e.g., from about 0.75 to about 3 mil (about 0.02 mm. to about 0.08 mm.)) polyester, polyethylene, or polypropylene film. Suitable polypropylene film can be obtained as the product designated JR-136 from the Food and Consumer Packaging Group of the James River Corporation of Cincinnati, Ohio.

If the substrate comprises the backsheet of a disposable diaper, the layer that takes the place of the backing may be comprised of any of the above materials, or similar materials. Typically, however, such a backsheet will be comprised of polyethylene.

The individual zones or layers of the female component 22 described above can be held together in any suitable manner. The entanglement zone 30 and spacing zone 32 are held in place on the backing 34. As long as the layers do not separate, it is not necessary for all three layers to be secured together, however. The spacing zone 32 can, therefore, be sandwiched between the entanglement zone 30 and the backing 34 without being secured to either, as long as the entanglement zone 30 and the backing 34 are secured in some manner.

The means used to hold the elements together (bonding means 44) must have several characteristics. The bonding means 44 must not create bonded regions, bonded areas 46, that occupy so much space that the bonded areas 46 interfere with the spaces needed for the hooks 28 of the mating hook component 24 to penetrate and occupy within the female component 22. The bonded areas 46 must also be sufficiently strong that the layers or zones of the female component 22 will not separate when the hooks 28 are disengaged.

The bonding means 44 may form bonded areas 46 that are either stronger or weaker than the structural elements that entangle the hooks 28. In preferred embodiments of the present invention, the bonded areas 46 are sufficiently strong relative to the strength of the structural elements that when relatively stiff hooks are used, the structural elements will fail instead of being pulled loose at an individual bonded area, bond site 46. If, on the other hand, the bond sites are the weakest element of the female component 22, each rigid hook 28 may be able to break several bond sites when the fastening device 20 is opened. This could cause entire structural components to be either nearly or completely torn away from the backing 34. If that occurs, the number of secured structural elements available to engage the hooks 28 will be significantly reduced. In addition, such loose structural elements will tend to interfere with the open space needed for the hooks 28 of the mating hook component 24 to penetrate.

The possible types of bonding means 44 may include, but are not limited to, stitching, ultrasonic bonds, adhesive bonds, and heat/pressure bonds.

In some cases, it may be preferable for ease of manufacture if the layers are autogenously secured. The term "autogenously", as used herein, means that the materials are secured to each other without the aid of a third material. Thus, the materials can be fused or melted to each other. This will typically occur when ultrasonic or heat/pressure bonds are used.

The type of bonding means 44 used may be limited to some extent by the types of materials in the different layers or zones of the female component 22. This is particularly true if the bonding means 44 are ultrasonic or heat/pressure bonds. When these two types of bonding means 44 are used, at least the materials comprising the entanglement zone 30 and the backing 34 should be compatible as far as the type of material and the melting temperature of the same are concerned. The term "compatible", as used herein, means that the materials are capable of being fused together.

When materials are described herein as being "similar", it is meant that the materials are generally comprised of the same compound, such as polypropylene. Similar materials may, however, comprise two different types of such a material (for instance, two different polypropylene materials).

The material comprising the spacing zone 32, however, does not have to be compatible with the materials comprising the entanglement zone 30 and the backing 34 (or if there is no backing, the substrate). The spacing zone 32 only needs to be held between the other two zones or layers; it need not be bonded to either. In fact, in some preferred embodiments, a material may be selected for the spacing zone 32 that is incompatible with the materials comprising the other two zones. Such a combination of materials may be advantageous because it may allow the structural elements of the spacing zone 32 (such as pellets) to remain unbonded and, thus, free to move between the other two zones. This will provide more room to accommodate the hooks 28 of the mating hook component 24.

When adhesive bonding means 44 are used, the materials comprising the entanglement zone 30 and the backing 34 do not necessarily have to be compatible. However, for ease of manufacture it may be preferable that these materials be capable of being bonded to the spacing zone 32 with the same adhesive.

The pattern that the bonded areas 46 are arranged in is also important. The bonding pattern may be continuous, intermittent, or spot bonded, depending on the type of materials used in the different zones. Some of the bonding patterns disclosed in U.S. patent application Ser. No. 07/355,065 entitled "Loop Fastening Material for Fastening Device and Method of Making Same" filed in the name of John R. Noel, et al. on May 17, 1989, may be suitable, provided the bonding pattern meets the criteria set forth herein.

A continuous bonding pattern is often preferred when the entanglement zone 30 comprises a nonwoven web because the fibers 36 in such a structure will be most likely to be secured in place.

An intermittent pattern that provides relatively small spaces or breaks between bonded areas 46, however, may also be suitable when nonwovens and certain other types of materials are used for the entanglement zone 30. A non-limiting example of an intermittent bonding pattern is provided in the upper left hand corner of FIG. 4B for purposes of illustration. The breaks 46' between the bonded areas 46 of such an intermittent pattern should be sufficiently small that there will be relatively few structural elements 36 in the entanglement zone 30 with unbonded loose ends. It is believed that an intermittent bonding pattern which has breaks 46' between bonded areas 46 that are less than or equal to the diameter of the smallest diameter structural elements in the entanglement zone 30 will be suitable. Larger breaks 46' between bonded areas may also be suitable. For instance, in some cases, the breaks 46' between bonded areas 46 could be as large as 1½ times, or even 5 times (or possibly even larger) the diameter of the smallest diameter structural elements in the entanglement zone 30.

If an intermittent bonding pattern is used, another important factor is the frequency of the breaks 46' in the pattern. The breaks 46' should not occur too frequently. If the breaks 46' occur too frequently, there will be too many fibers 36 with unbonded loose ends. It is preferred that the bonded areas 46 are longer (occupy more area) than the breaks 46' along each intermittent line in the bond pattern.

If the entanglement zone 30 comprises a structure that has more inherent integrity (for instance, if a woven fabric or a screen is used for the entanglement zone 30), the entanglement zone 30 may be spot bonded to the other zones.

The pattern of the bonded areas 46 is preferably regular. Suitable bonding patterns (particularly for nonwovens), include continuous lines. Such lines can be curved, e.g., sinusoidal, or they can be arranged in the form of grids that define different geometrical shapes such as squares, rectangles, hexagons, diamonds, and circles. This will provide the female component 22 with relatively uniform holding characteristics.

The bonded areas 46 preferably have certain additional characteristics if the entanglement zone 30 comprises a nonwoven material. In such a case, the bonded areas 46 in the bond pattern must be sufficiently close together that the fibers 36 of the nonwoven material will have relatively few unbonded loose ends. In order to ensure that this happens, the distance between bonded areas 46 should preferably be less than the average length of fibers 36 in the entanglement zone 30, more preferably, less than or equal to about one-half the length of the fibers 36 in the entanglement zone 30. (The distance between bonded areas 46 specified refers to the spaces other than the breaks 46' in an intermittent bonding pattern.)

Figure 4B:
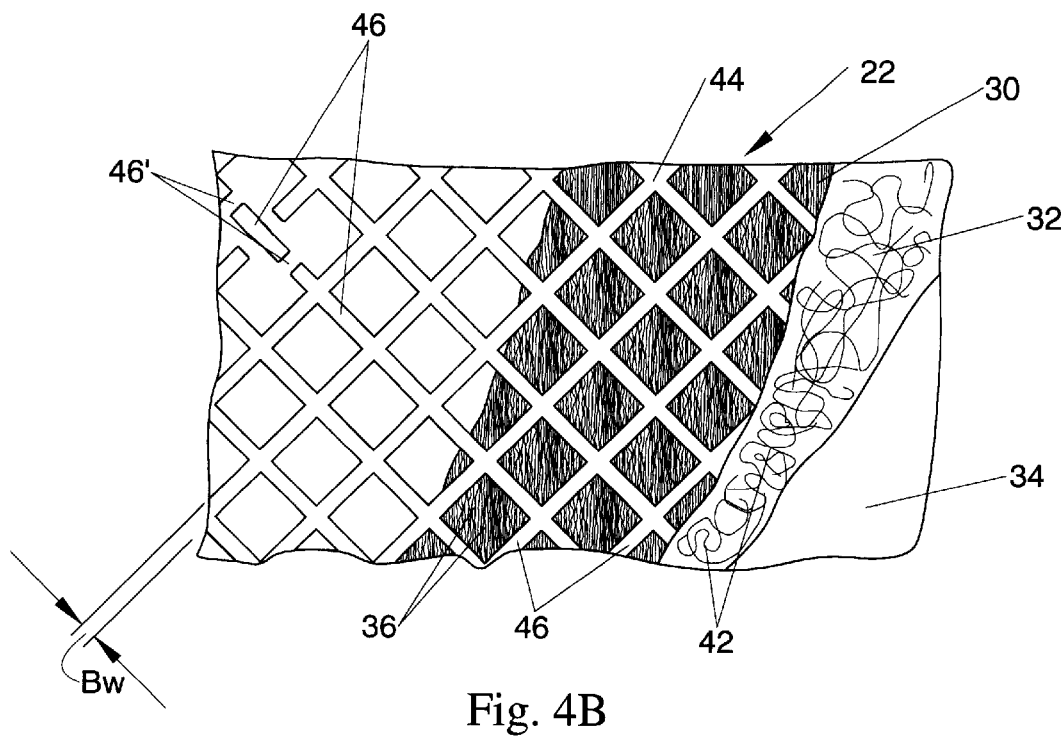
Figure 4C:
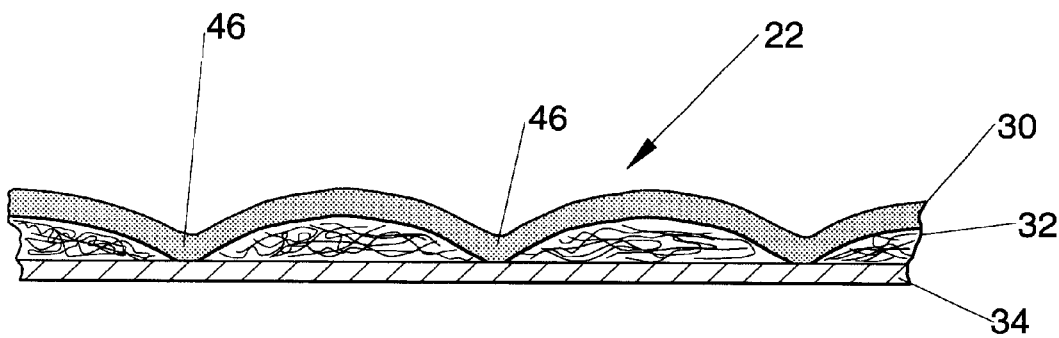
FIG. 4C is a side view of the female component shown in FIGS. 4A and 4B which shows the bonding between the zones of the same in a slightly less schematic form.

A preferred bonding pattern is the diamond-shaped pattern shown in FIG. 4B. The "diamonds" in the "diamond-shaped" pattern are generally square elements. These elements are rotated approximately 45 degrees to give them the appearance of diamonds. The dimensions of the pattern should be such that the distance between bonded areas 46, in at least some portion of the area between bonded areas, is greater than the projected plan view dimensions of the heads 38 of the hooks 28 of the mating hook component 24.

Examples of diamond-shaped bonding patterns which are suitable for use with some of the hook components described herein are as follows. These include, but are not limited to patterns having sides that measure about ¼ inch×¼ inch (about 0.6 cm.×0.6 cm.); about ⅜ inch×⅜ inch (about 1 cm.×1 cm.); about ½ inch×½ inch (about 1.3 cm.×1.3 cm.); and, about ¾ inch×¾ inch (about 2 cm.×2 cm.).

The width of the bonded areas 46 in cross-section, $B_w$, shown in FIG. 4B, can vary. In the examples of the diamond-shaped bonding patterns described above, a suitable bond width (measured at the backing 34) is between about 0.03 inch and about 0.05 inch (about 0.76 mm. and about 1.3 mm.).

The cross-sections of the bonds shown in FIGS. 3 and 4A are shown to be tapered in width so that they become narrower from the first surface 31 of the female component 22 to the second surface 33. The tapering of the width of the bonds in cross-section is primarily of interest in relation to the cost and life of the patterned rolls used to form such bonds in the method of making the female component 22. (For instance, it may be less expensive to manufacture rolls having patterned surfaces tapered to form such bonds.)

In one particularly preferred embodiment of the female component 22 of the present invention, the entanglement zone 30 is a first nonwoven web. The first nonwoven web is a spunbonded nonwoven web. The first nonwoven web has a basis weight of between about 7 and about 15 grams/square yard (between about 8.5 and about 18 grams/square meter). The first nonwoven web is comprised of continuous filament polypropylene fibers that have a denier of between about 3 and about 6, most preferably, about 3. The fibers are preferably primarily oriented in a single direction. In addition, in this preferred embodiment, the spacing zone 32 also comprises a nonwoven web, and the fibers in the entanglement zone 30 are finer than those in the spacing zone 32.

In the preferred embodiment described above, the spacing zone 32 is a second nonwoven web. The second nonwoven web is a carded nonwoven web which has a basis weight of between about 7 and about 30 grams/square yard (about 8.5 to about 36 grams/square meter). The second nonwoven web is comprised of polypropylene fibers having a length of between about 1.5 inches and about 2.5 inches (between about 4 cm. and about 6 cm.) and a denier of between about 6 and 15, most preferably, about 9. The fibers of the spacing zone 32 are preferably crimped with at least about 10 crimps/inch (about 4 crimps/cm.), most preferably with at least about 14 crimps/inch (an average of about 5.5 crimps/cm.). The crimped fibers are preferably randomly oriented in the spacing zone 32. The spacing zone 32 is preferably also resilient.

The composite or total basis weight of both the entanglement zone 30 and the spacing zone 32 should be between about 15 and about 35 grams/square yard (about 18 to about 42 grams/square meter). (This total basis weight could also include the backing 34 since the backing will typically have a relatively low basis weight.)

In the particularly preferred embodiment described above, the backing 34 is preferably a polypropylene film. The three layers, the entanglement zone 30, the spacing zone 32, and the backing 34 are secured with the preferred diamond-shaped bonding pattern shown in FIG. 4B, and described in greater detail above.

FIGS. 4A to 23 show various alternative embodiments of the multi-layer female component 22 of the present invention.

FIGS. 4A and 4B are a side view and a partially cut-away plan view, respectively, of a second alternative embodiment of the multi-layer female component 22 of the present invention. In this second alternative embodiment, the fibers of the nonwoven web used for the entanglement zone 30 and the fibers of the nonwoven web used for the spacing layer 32 are of the same thickness. (Rather than fibers with large diameters being used for the spacing zone 32, and finer fibers for the entanglement zone 30 as shown in FIGS. 1–3).

FIG. 5 shows a third alternative embodiment of the female component 22 in which the entanglement zone 30 comprises a woven fabric rather than a nonwoven web.

Figure 6:
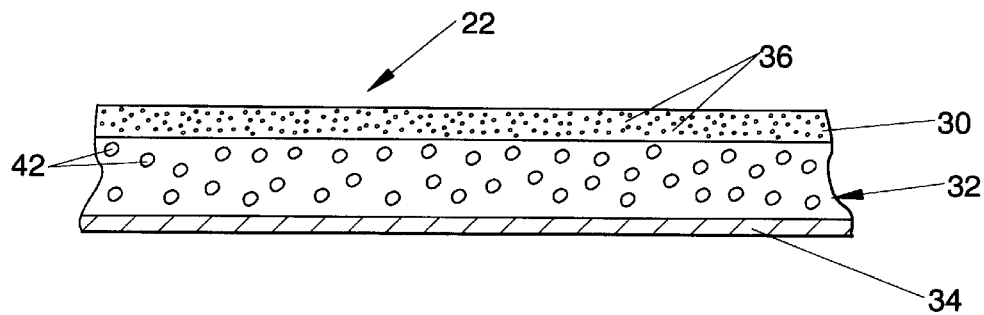
FIGS. 6 and 7 are simplified schematic side views of alternative embodiments of the multi-layer female component in which the spacing zone comprises a loose pellet-like material.
Figure 7:
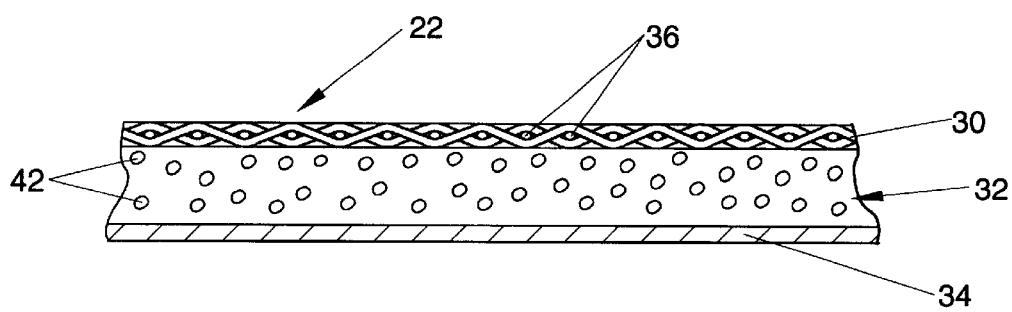

FIGS. 6 and 7 show a fourth alternative embodiment of the female component 22 in which the spacing zone 32 is a loose pellet-like material rather than a nonwoven material as in the case of the previous embodiments. The structural elements of such an embodiment comprise pellets 42. FIG. 6 shows a version of this alternative embodiment having a nonwoven entanglement zone 30. FIG. 7 shows a version in which the entanglement zone 30 is a woven fabric.

FIGS. 8–11 show a fifth alternative embodiment of the female component 22 in which the spacing zone 32 is a net, screen or geometric screen, scrim, or similar element. The terms "net", "screen", "geometric screen", "scrim", as used herein, typically refer to structures comprised of ribs, filaments, strands, or the like, in which the junctures between such structural elements 42 are integral with the structural elements. (It is also within the scope of the present invention, however, for the spacing zone to comprise structures having junctures which are not integral with the structural elements.) For simplicity, the type of structure shown in FIGS. 8–11 will be referred to as a "screen".

In these embodiments, the screen 32 spaces the entanglement zone 30 away from the backing 34. The hooks 28 are stored in the spaces between the structural elements 42 of the screen 32.

The screen 32 may have structural elements 42 that are flexible enough to move out of the way of the hooks 28 of the mating hook component 24. In alternative cases, the screen 32 may be so rigid that no such movement is possible. If the structural elements 42 of the screen 32 are not capable of moving, the hooks 28 will simply not be stored in the areas occupied by the structural elements 42.

The screen 32 may have structural elements 42 that are small enough to be entangled by the hooks 28 of the mating hook component 24. In other alternatives, the structural elements 42 may be larger than the gap 41 defined by the heads 38 of the hooks 28 so that no such entanglement is possible.

Typically, the structural elements 42 of the screen 32 that run in each direction will be of approximately the same diameter. The structural elements 42 of the screen 32 that are oriented in different directions have, however, been shown in FIGS. 8–11 to have different diameters for clarity of illustration. The structural elements 42 which run parallel to the plane of the paper have been shown as being of a slightly smaller diameter than the structural elements 42 that run in a direction into the plane of the paper. It is possible that a suitable screen could be formed with structural elements of different diameters.

FIGS. 8–11 show four examples of possible combinations of layers of material and bonding between the layers when the spacing zone 32 is a screen. In all of the embodiments shown in FIGS. 8–11, the entanglement zone 30 comprises either a woven fabric or a nonwoven web, and the backing 34 is a film. There are two basic types of bonding means 44 shown schematically in FIGS. 8–11, heat/pressure bonding means and adhesive applied to both sides of the screen 32.

Figure 8:
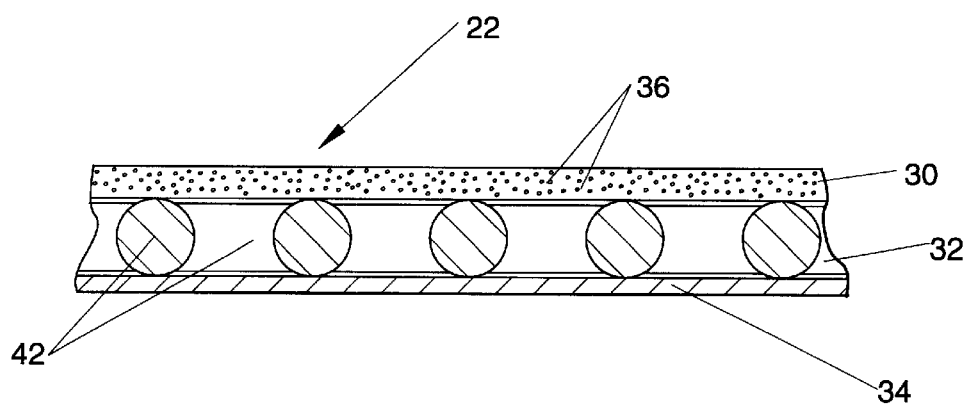
FIGS. 8 and 9 are side views of alternative embodiments of the multi-layer female component in which the spacing zone comprises a screen bonded by heat/pressure bonds to the adjacent layers.
Figure 9:
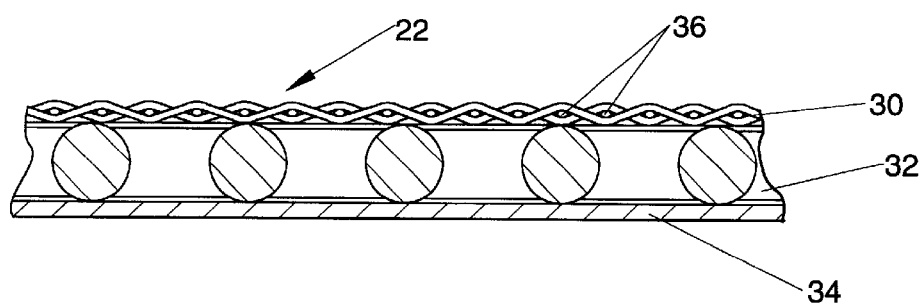
Figure 10:
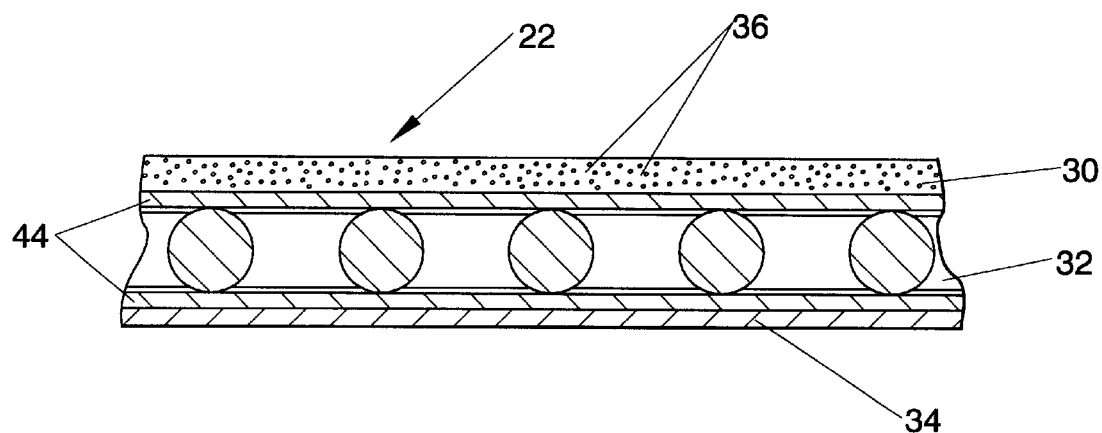
FIGS. 10 and 11 are side views of alternative embodiments of the multi-layer female component in which the spacing zone comprises a screen bonded to the adjacent layers by an adhesive.
Figure 11:
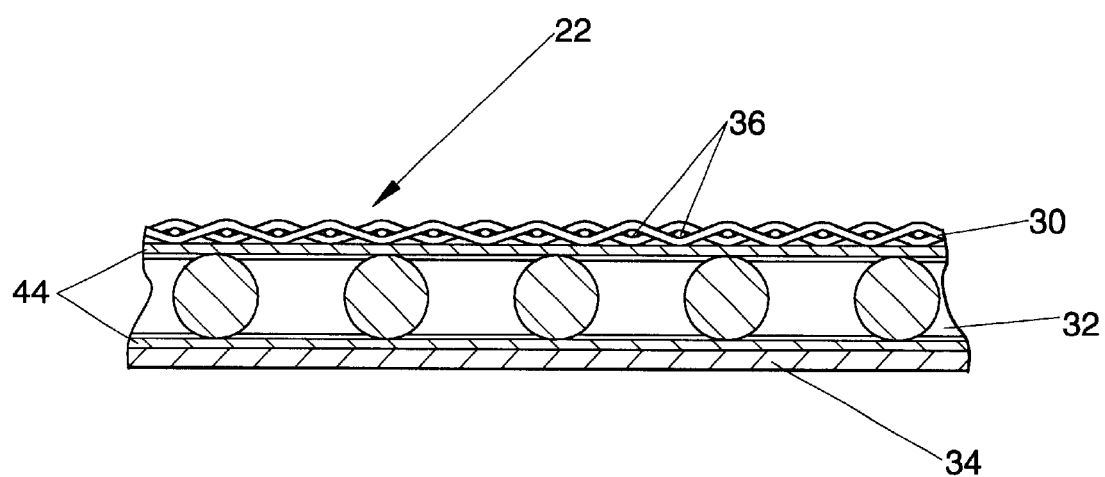

FIG. 8 shows a female component 22 that comprises a nonwoven entanglement zone 30 and a film backing 34 bonded to a screen that serves as the spacing zone 32 by heat/pressure bonds. FIG. 9 shows a female component 22 that comprises a woven entanglement zone 30, a screen spacing zone 32, and a film backing 34 bonded by heat/pressure bonds. FIG. 10 shows a female component 22 that comprises a nonwoven entanglement zone 30, a screen spacing zone 32, and a film backing 34 bonded by an adhesive. FIG. 11 shows a female component 22 that comprises a woven entanglement zone 30, a screen spacing zone 32, and a film backing 34 bonded by an adhesive. Any of the other materials and types of bonding means 44 described herein may be used to form additional embodiments.

FIGS. 12–17 show a sixth alternative embodiment of the female component 22 of the present invention. In the sixth alternative embodiment, the film backing 34 is eliminated. The different zones of the female component are formed by stacking one of the materials generally used in the spacing zone 32 on top of one of the materials generally used as the entanglement zone 30, or vice versa, to form a laminate. This laminate is then folded over on top of itself so that the spacing zone material faces other spacing zone material. The folded laminate may then be bonded to form the female component 22. (In the process of making this embodiment, the fold is oriented in the machine direction.)

As shown in the drawings, after folding, the spacing zone 32 material is disposed in two layers. The layers of spacing zone 32 material are sandwiched between layers of the entanglement zone material. One layer of the entanglement zone material is designated 30 as forming the entanglement zone, and the other layer is designated 34 as forming a backing.

This folding process may form a spacing zone 32 that has characteristics that make it react as if it has either more structural elements or more loft than a single layer of spacing zone 32 material of equivalent thickness. This is especially the case when the material used in the spacing zone 32 is a woven or nonwoven fabric, a screen, or the like (typically not loose particles). The folding usually causes the structural elements of different portions of the spacing zone material to be slightly misaligned or offset with respect to each other at the interface between the folded portions. That is, there is a "mismatch" of structural elements so they are not in direct alignment. This often provides a female component 22 that exhibits increased resistance to the removal of the hooks 28 of the mating hook component 24.

There are various combinations of this sixth folded embodiment depending on the material chosen for the respective zones or layers. These include, but are not limited to the versions shown in the drawings. The drawings are merely intended to show some examples of possible structures.

Figure 12:
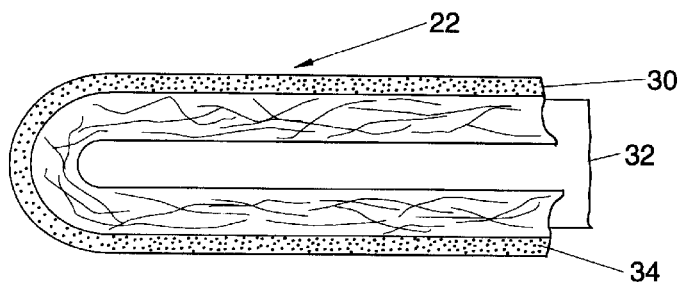
FIGS. 12–17 are side views of alternative embodiments of the multi-layer female component that are formed by forming a laminate, and then folding the laminate on top of itself.

FIG. 12 shows a female component 22 in which the material used for the spacing zone 32 is a nonwoven web and the material used for the entanglement zone 30 is another nonwoven web. The laminate before folding comprises a nonwoven material stacked on top of another nonwoven material. After folding, the female component 22 comprises a nonwoven entanglement zone 30 and a nonwoven backing 34 with two nonwoven layers of spacing zone 32 material in between.

Figure 13:
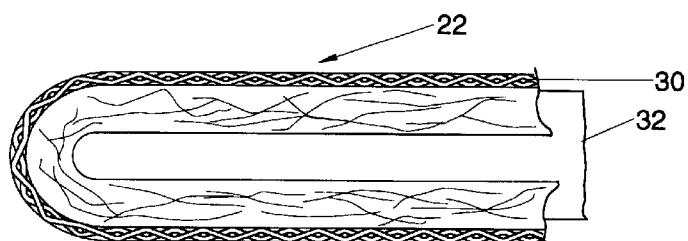

FIG. 13 shows a female component 22 in which the spacing zone 32 material is a nonwoven web and the entanglement zone 30 material is a woven fabric. The laminate before folding comprises a nonwoven material stacked on top of a woven material. After folding, the female component 22 comprises a woven entanglement zone 30 and a woven backing 34 with two layers of nonwoven spacing zone 32 material in between.

Figure 14:
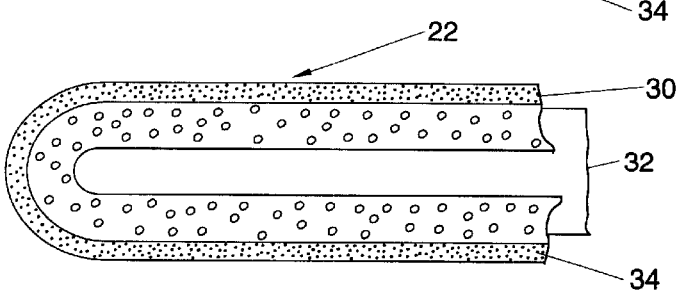

FIG. 14 shows a female component 22 in which a loose material is used for the spacing zone 32 and the entanglement zone 30 material is a nonwoven web. The laminate before folding comprises layer of loose material on top of a nonwoven material. After folding, the female component 22 comprises a nonwoven entanglement zone 30 and a nonwoven backing 34 with a loose material in between.

Figure 15:
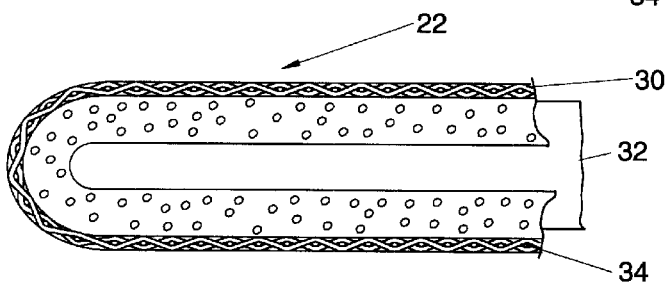

FIG. 15 shows a female component 22 in which a loose material is used for the spacing zone 32 and the entanglement zone 30 material is a woven fabric. The laminate before folding comprises layer of loose material on top of a woven material.

After folding, the female component 22 comprises a woven entanglement zone 30 and a woven backing 34 with a loose material in between.

Figure 16:
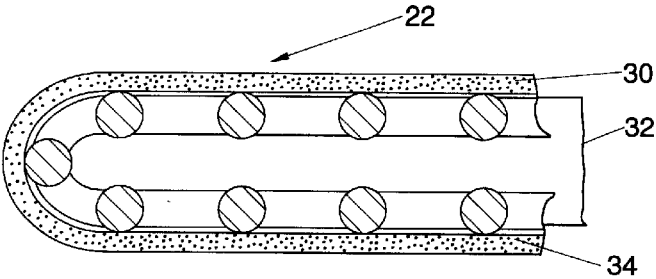

FIG. 16 shows a female component 22 in which material used for the spacing zone 32 is a screen and the material used for the entanglement zone 30 is a nonwoven web. The laminate before folding comprises a screen placed on top of a nonwoven material. After folding, the female component 22 comprises a nonwoven entanglement zone 30 and a nonwoven backing 34 with two thicknesses of the screen in between.

Figure 17:
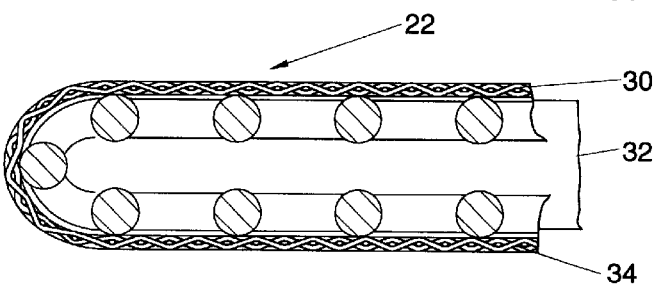

FIG. 17 shows a female component 22 in which the material used for the spacing zone 32 is a screen and the material used for the entanglement zone 30 is a woven fabric. The laminate before folding comprises a screen placed on top of a woven fabric. After folding, the female component 22 comprises a woven entanglement zone 30 and a woven backing 34 with two thicknesses of the screen in 30 between.

There are still other versions of the sixth folded embodiment.

For instance, an embodiment could be constructed in which only one of the materials that forms the female component is folded. A non-limiting example of this type of structure would occur if loose particles are used for the spacing zone 32 and a nonwoven web is used for the entanglement zone. In such a case, the loose particles could be distributed across only half of the width of the nonwoven web. The other half of the nonwoven web could be folded on top of the loose particles. This would form a female component in which only one of the materials is folded.

In another version of such an embodiment, the material that forms the top layer of the laminate could be folded instead. For instance, a nonwoven web could be placed on top of a woven material. The nonwoven web could have twice the width of the woven material. The nonwoven web could then be folded over on top of itself and secured to the woven material to form a female component.

Numerous other variations are possible. For instance, the folded layer could be an intermediate layer. Thus, the sixth embodiment could be any embodiment in which at least one of the layers is folded. All such versions are capable of being understood from the above description and the examples shown in the drawings.

FIGS. 18–23 show a seventh alternative embodiment of the present invention. In the seventh alternative embodiment, a layer of the same material used in the entanglement zone 30 is used in place of the film backing. There are various combinations of the seventh embodiment depending on the material chosen for the respective zones or layers. These include, but are not limited to the versions shown in the drawings. As before, the drawings are merely intended to provide some examples.

Figure 18:
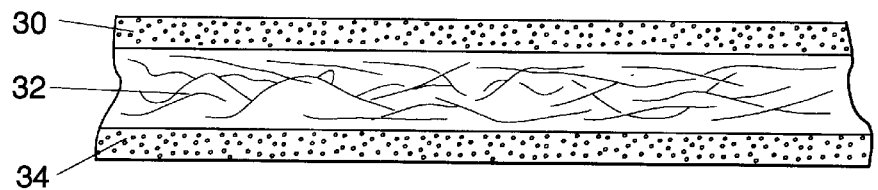
FIGS. 18–23 are side views of alternative embodiments of the multi-layer female component in which the same type of material is used for both the entanglement zone and the backing.
Figure 19:
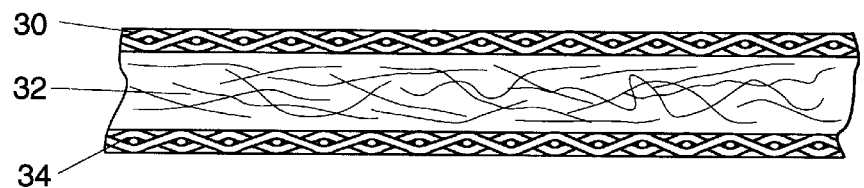
Figure 20:
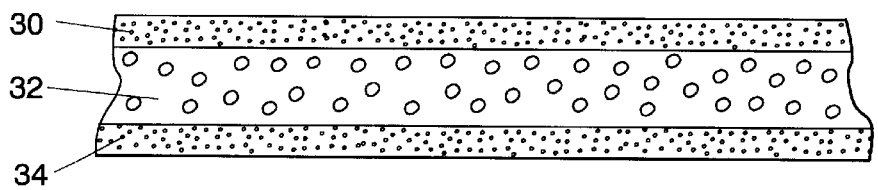
Figure 21:
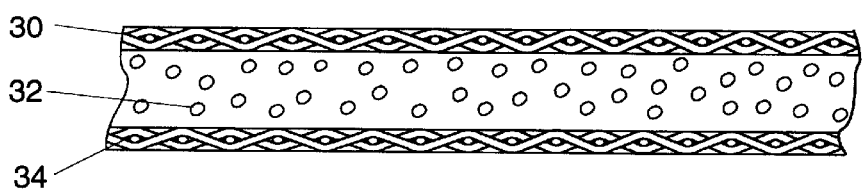
Figure 22:
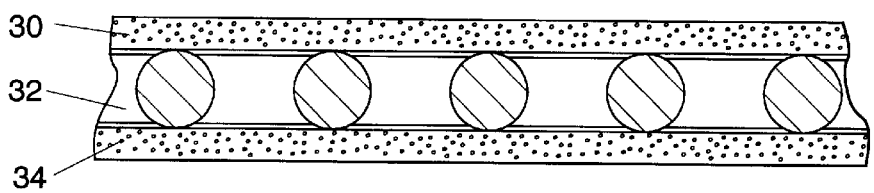
Figure 23:
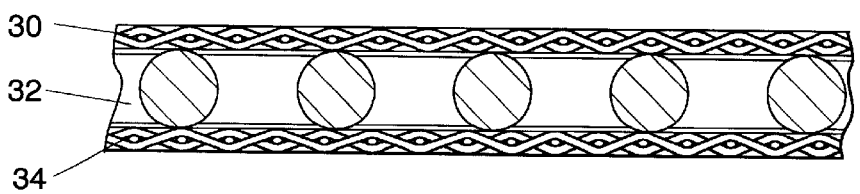

FIG. 18 shows a version of the seventh embodiment in which the female component 22 comprises a lofted nonwoven material between two layers of less lofted nonwoven material. FIG. 19 shows a version of the seventh embodiment in which the female component 22 comprises a lofted nonwoven material as an intermediate layer between two layers of woven material. FIG. 20 shows a version of the seventh embodiment in which the female component 22 comprises a loose material as an intermediate layer between two layers of nonwoven material. FIG. 21 shows a version of the seventh embodiment in which the female component 22 comprises a loose material as an intermediate layer between two layers of woven material. FIG. 22 shows a version of the seventh embodiment in which the female component 22 comprises a screen as an intermediate layer between two layers of nonwoven material. FIG. 23 shows a version of the seventh embodiment in which the female component 22 comprises a screen as an intermediate layer between two layers of woven material.

It should be understood that the embodiments of the multi-layer female component 22 of the present invention described above are for purposes of illustration only. It is apparent that there are many possible combinations of the different zones or layers described herein. These combinations are capable of being understood from the description provided above and the examples set forth in the drawings. The multi-layer female component 22, however, is not limited to the specific embodiments shown in the drawings.

The present invention provides a low-cost female component for a refastenable fastening device. The female component 22 makes more efficient use of raw materials than existing fastening devices by utilizing reduced amounts of expensive materials and by providing a female component in which the different functions served by conventional loop components are served by separate layers. Each layer or zone has certain of the desired individual characteristics for entangling and holding the hooks of the mating hook component.

The first zone, entanglement zone 30, admits and engages at least some of the hooks of the complementary hook component. The second zone, spacing zone 32 provides space for the hooks to occupy after they have been admitted by the entanglement zone. The backing 34 provides a foundation for the entanglement and spacing zones 30 and 32. Because the spacing zone 32 is not required to serve the function of entangling the hooks, less expensive materials can be used in the spacing zone 32. This is a departure from existing loop components in which the same, relatively expensive raw material is used for the entire composition of the loop component.

Thus, the fastening device 20 is especially useful on such disposable articles as packaging, disposable absorbent articles, disposable wraps, and the like. The female component 22 is more suited for disposable articles since the fastening device on a disposable article is opened and closed far fewer times than on reuseable articles. The female component 22 generally only needs to be strong enough to provide a limited number of secure closures (for example, a maximum of about 10–20 closures).

It should be noted, however, that the female component 22 can be made much stronger for use on durable articles or for any other contemplated use. This can be done by, for example, increasing the diameter or denier of the structural elements of the entanglement zone 30, more strongly securing the structural elements to the backing 34 or increasing the density of the structural elements relative to the number of hooks 28. However, these changes also increase the cost of the female component 22.

The female component 22 can also be used in conjunction with lower cost hook components having more brittle hooks. In such cases, instead of the hooks bending to release from mechanical entanglement with the structural elements, the structural elements of the female component 22 may advantageously break or serve as a "failure mechanism" to allow the disengagement of the hooks upon opening the fastening device.

3. The Mating Hook Component

The mating hook component 24 is shown in numerous places in the drawings.

The term "hook component", as used herein, is used to designate the portion of the fastening device 20 having engaging elements, such as hooks 28. The term "hook" is nonlimiting in the sense that the engaging elements may be in any shape known in the art as long as they are adapted to engage a complementary loop fastening material or the female component 22 of the present invention.

The hook component 24 comprises a base 26 having a first surface 27 and a second surface 29 and a plurality of engaging elements 28 extending from the first surface 27 of the base 26. Each of the engaging elements 28 are shown to preferably comprise a stem 40 supported at one end on the base 26 and an enlarged head 38 positioned at the end of the stem 40 opposite of the base 26.

The hook components 24 used with the multi-layer female component 22 of the present invention can be conventional, commercially available hook materials. The hook component 24, however, is not limited to conventional materials with flexible, resilient hooks. Suitable hook components can have less expensive, more brittle hooks.

The hook components 24 used with the multi-layer female component 22 can have hooks 28 with blunt heads 38. The portion of the heads 38 of the hooks 28 that are blunt is that portion designated as the apex 39 of the hook 28 in FIG. 3B. The apex 39 will first come in contact with the female component 22 of the present invention when the female component 22 and the complementary hook component 24 are placed in face-to-face relationship with each other. This portion is referred to as the apex of the hook 28 because it is portion of the hook 28 that is greatest perpendicular distance from the base 26 of the hook component 24. The term "blunt", as used herein, means that the apex 39 is dull in that it forms an edge or point that is not sharp. The apex 39 of a hook 28 having a blunt head can be generally rounded, flat, or any other shape that does not provide a sharp point.

The female component 22 of the present invention, thus, does not require specially-made rigid, sharp hooks to be used. It is, however, possible for hooks of all configurations, including such sharp hooks to be used with the female component 22.

A suitable hook component 24 may comprise a number of shaped engaging elements projecting from a woven backing such as the commercially available material designated "Scotchmate" brand No. FJ3402 available from Minnesota Mining and Manufacturing Company, St. Paul, Minn. The engaging elements may have any shape known in the art such as hooks, "T's", mushrooms, or any other shape. A particularly preferred hook component is described in U.S. Pat. No. 4,846,815 entitled "Disposable Diaper Having An Improved Fastening Device" which issued to C. L. Scripps on Jul. 1, 1989. Another particularly preferred hook component is described in European Patent Application Publication Number 0 381 087 A1 entitled "Refastenable Mechanical Fastening System and Process of Manufacture Therefor", published Aug. 8, 1990 by Dennis A. Thomas. The disclosure of these patent publications, and all other patents, patent applications, and publications referred to in this application are hereby incorporated by reference herein.

The shape of the cross-section of the shank is not critical. However, the shank is preferably tapered to decrease in cross-section as the distal end of the shank and engaging means of the prong are longitudinally and laterally approximated. This arrangement provides a corresponding decrease in the moment of inertia of the shank and engaging means resulting in a prong of more nearly constant stress when separation forces are applied to the fastening system, and thereby diminishes the quantity of superfluous material incorporated into the prong.

It is advantageous to dispose the prongs in rows, so that each prong is generally equally spaced from the adjacent prong. Generally, each machine direction and cross-machine direction row of prongs should be equally spaced from the adjacent machine direction and cross-machine direction rows of prongs, to provide a generally uniform stress field throughout the fastening system and the receiving surface when separation forces are applied to the fastening system and the receiving surface. The array of prongs may be of any pattern and density as desired, to achieve the peel and shear strengths required for the particular application of the fastening system. The engaging means of each prong of the fastening system may laterally extend substantially in the same direction, if a laterally unidirectionally oriented peel strength is desired, or may be randomly oriented to provide substantially isotropic peel strengths in any lateral direction.

(It should be understood that the various portions of the hook components may be described in these references with slightly different terminology than is used herein. However, the drawings and elements contained herein can be compared to those of the references to readily locate the corresponding portions of the hook components described in those publications.)

The hook component 24 may be manufactured from a wide range of materials. Such suitable materials include, but are not limited to nylon, polyester, polypropylene or any combination of these or other materials.

The size of the heads 38 of the hooks 28, as noted above, determines the open space required between the structural elements of the entanglement and spacing zones 30 and 32. Some non-limiting examples of sizes of hooks 28 that are useful with the female component 22 of the present invention are provided below.

One suitable hook component 24 has T-shaped hooks 28 with the following dimensions. The length of the head L, is about 1 mm.; the width W, is about 0.2 mm.; and the height h1, is about 0.3 mm. If this type of hook component is used, the openings between the structural elements of the entanglement and spacing zones 30 and 32, should be (or should readily spread without being pierced to) dimensions of slightly greater than about 0.2 mm by about 1 mm. The caliper of the spacing zone 32 should be greater than about 0.3 mm.

Another suitable hook component 24 hooks 28 in the shape of an upside down letter "J". (The hooks 28 of such a hook component 24 could also be said to resemble candy canes.) In other variations, such a hook could resemble an upside down upper case letter "L". Such hooks could have the following dimensions. The length of the head L, is about 0.5 mm.; the width W, is about 0.2 mm.; and the height h1, is about 0.3 mm. Thus, if this type of hook component is used, the openings between the structural elements of the entanglement and spacing zones 30 and 32, should be (or should readily spread without being pierced to) dimensions of slightly greater than about 0.2 mm. by about 0.5 mm. The caliper of the spacing zone 32 should be greater than about 0.3 mm.

Still other hook components 24 could have hooks as small as ½ to ¼, or smaller than the hooks described above.

4. Examples of Uses of the Refastenable Fastening Device

The fastening device 20 of the present invention is especially useful as a fastening device for disposable articles, particularly disposable absorbent articles.

The term "disposable absorbent article", as used herein, refers to articles which absorb and contain body exudates. More particularly, the term refers to articles which are placed against or in proximity to the body of the wearer to absorb and contain the various exudates discharged from the body. The term "disposable" means that such articles are intended to be discarded after a single use (i.e., they are not intended to be laundered or otherwise reused). Examples of disposable absorbent articles include diapers, incontinent garments, sanitary napkins, bibs, bandages, and the like.

Figure 24:
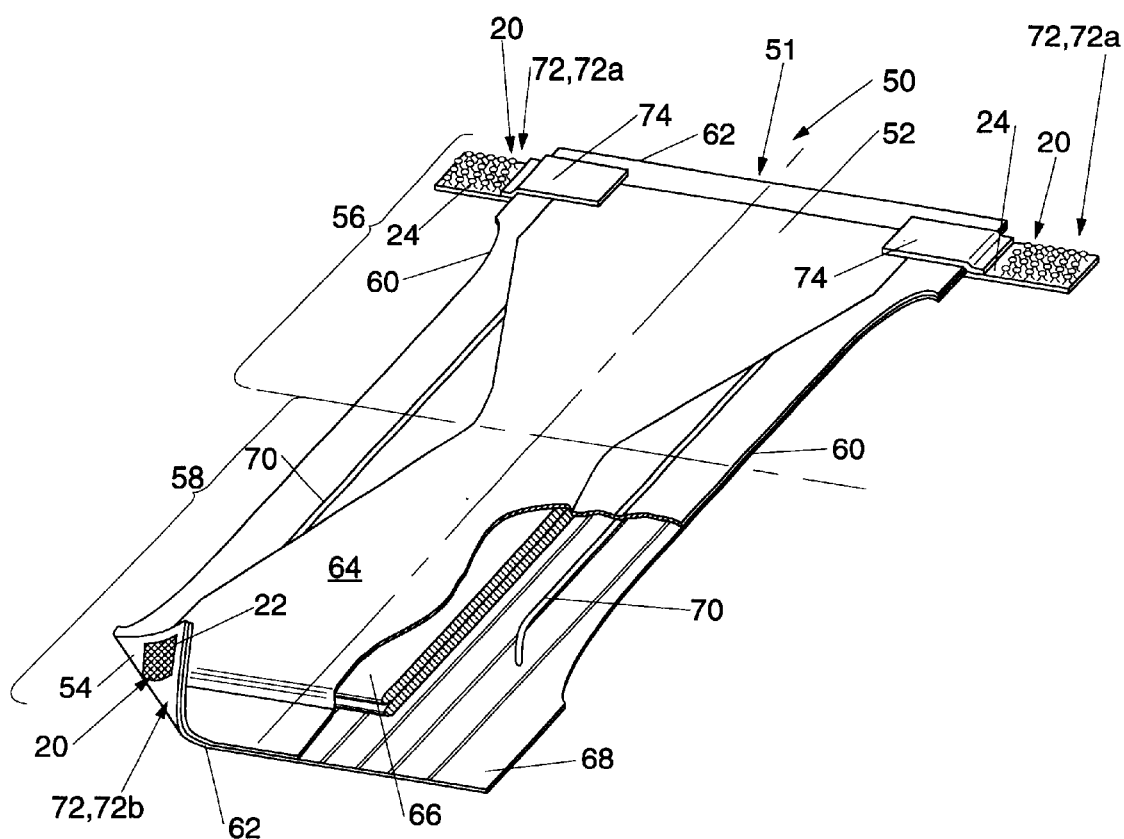
FIG. 24 is a partially cut-away perspective view of a disposable diaper that includes the fastening device of the present invention.

The fastening device 20 is shown in FIG. 24 positioned on a preferred embodiment of a disposable absorbent article, disposable diaper 50. The term "diaper", as used herein, refers to a garment generally worn by infants and incontinent persons that is drawn up between the legs and fastened about the waist of the wearer.

The disposable diaper 50 has an inside surface (or body surface) 52, intended to be worn adjacent to the body of the wearer. The diaper 50 has an outside surface (or garment surface) 54 intended to be placed adjacent the wearer's clothing when the diaper 50 is worn. The diaper 50 has two waist regions, which are designated as first waist region 56 and second waist region 58. The diaper 50 has two spaced apart longitudinal edges 60 and two spaced apart transverse or end edges 62.

The disposable diaper 50 comprises a body portion 51 and a mechanical fastening system, such as tape tab fastening system, or simply "fastening system" 72. The body portion 51 of the diaper 50 comprises a liquid pervious topsheet 64, an absorbent core 66, a liquid impervious backsheet 68, and elastic members 70. The topsheet 64, the absorbent core 66, the backsheet 68, and the elastic members 70 may be assembled in a variety of well known configurations.

Several examples of the kinds of diapers to which the present invention is readily adapted are shown in U.S. Pat. No. Re. 26,151 entitled "Disposable Diaper" which reissued to Robert C. Duncan, et al., on Jan. 31, 1967; U.S. Pat. No. 3,860,003 entitled "Contractible Side Portions For Disposable Diapers" which issued to K. B. Buell on Jan. 14, 1975; U.S. Pat. No. 4,695,278 entitled "Absorbent Article Having Dual Cuffs", issued to Michael I. Lawson on Sep. 22, 1987; U.S. Pat. No. 4,834,735 entitled "High Density Absorbent Members Having Lower Density And Lower Basis Weight Acquisition Zones" which issued to Miguel Alemany, et al. on May 30, 1989; and U.S. Pat. No. 4,909,803 entitled "Disposable Absorbent Article Having Elasticized Flaps Provided With Leakage Resistant Portions" which issued to Mohammed I. Aziz, et al. on Mar. 20,1990. It should be understood, however, that the fastening device 20 of the present invention is not limited to use with any specific diaper structure or configuration.

The fastening system 72 of the diaper 50 preferably comprises the fastening device 20 of the present invention, among other elements. The fastening system 72 may be in the form of any of the well known configurations and constructions currently in use. Preferably, the fastening system 72 is a tab fastening system, preferably a tape tab fastening system.

The tape tab fastening system can comprise any of the well known tape tab configurations and constructions currently in use. A preferred tape fastening system uses the Y-tape tab described in detail in U.S. Pat. No. 3,848,594 entitled "Tape Fastening System For Disposable Diaper" which issued to K. B. Buell on Nov. 19, 1974. Alternatively preferred tape fastening systems are described in detail in European Patent Application 0 233 704-A, entitled "Disposable Diaper Having Wide Tapered Fastening Tapes" published Aug. 26, 1987 by H. R. Burkhart and Kenneth B. Buell; previously referenced U.S. Pat. No. 4,846,815 issued to C. L. Scripps; and U.S. Pat. No. 4,963,140 entitled "Mechanical Fastening Systems With Disposal Means for Disposable Absorbent Articles" which issued to Anthony J. Robertson, et al. on Oct. 16, 1990.

In still other preferred embodiments, the female component 22 of the fastening system 72 could comprise an element, such as a patch located on one of the surfaces of the body portion of a diaper (or other suitable places) to form an "inner fastening member" as described in U.S. Pat. No. 4,699,622 entitled "Disposable Diaper Having An Improved Side Closure" which issued to J. W. Toussant, et al. on Oct. 13, 1987.

The tape fastening system 72 shown in FIG. 24 is a non-limiting example of, the type of fastening system which can use the fastening device 20 of the present invention. The tape fastening system 72 comprises a tape tab 74 having a first fastening element 72a located thereon, and a second fastening element (or "landing member") 72b. The second fastening element 72b is mechanically engageable with the first fastening element 72a.

Preferably, the first fastening element 72a comprises a hook component 24. The hook component 24 provides hooks 28 that extend from the tape tab 74. In a preferred embodiment of the disposable diaper 50, the second fastening element 72b comprises the multi-layer female component 22 of the present invention. In other embodiments, the positions of the components of the fastening device 20 of the present invention could be reversed so that the first fastening element 72a comprises the multi-layer female component 22 and the second fastening element 72b comprises the hook component 24.

As shown in FIG. 24, the multi-layer female component 22 is preferably located on the second waist region 58 of the diaper 50. In a preferred embodiment of the disposable diaper 50, a plurality of the structural elements 36 of the entanglement zone 30 are aligned in a single direction. The female component 22 is oriented so that the structural elements 36 of the entanglement zone 30 extend essentially parallel to the longitudinal edges 60 of the diaper 50. This orientation aligns the structural elements generally perpendicular to the direction of shear forces applied to the fastening device 20 during use. In this configuration the structural elements 36 provide the maximum peel and shear force resistance. The female component 22 may, however, be oriented on the second waist region 58 in any manner with the structural elements 36 extending in any direction.

In use, the diaper 50 is applied to the wearer by positioning the first waist region 56 under the wearer's back and drawing the remainder of the diaper 50 between the legs of the wearer so the second waist region 58 is positioned across the front of the wearer. The tape tabs 74 are then positioned adjacent to the female component 22 positioned on the outside surface 54 of the second waist region 58 so the hooks 28 which are disposed on the tape tab 74 will engage the female component 22 to form a side closure.

Method of Making the Female Component

Figure 25:
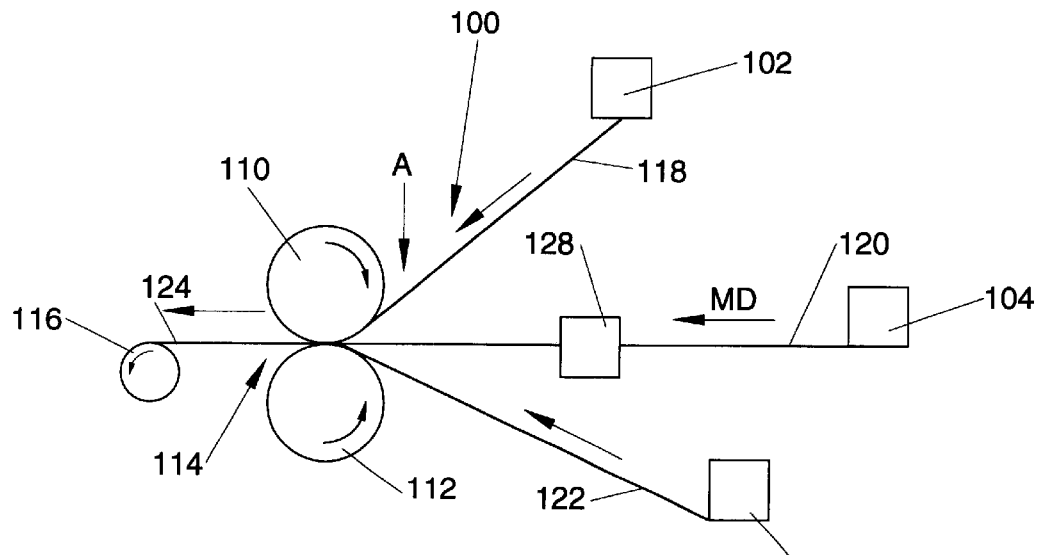
FIG. 25 is a schematic side view of a process for making the multi-layer female component of the present invention.

The method or process of making the female component 22 of the present invention is shown in schematic form in FIG. 25.

The apparatus for making the multi-layer female component 20 of the present invention is designated 100. The apparatus 100 includes a first supply means 102, a second supply means 104, and a third supply means 106, for feeding into the system the materials that will comprise the zones or layers of the multi-layer female component 22.

The apparatus 100 may also include an element that provides an embossed surface, embossed roll 110 (which may be patterned), and an anvil member, such as anvil roll 112. The embossed roll 110 and anvil roll 112 define a nip 114 between them. The nip 114 is where the laminae of the webs or other materials fed into the system are bonded together. The bonded web 124, may then travel to a take-up roll 116, where it is wound for subsequent use. The apparatus 100 may further include an optional folding means, such as folding bars 108, shown in enlarged scale in FIG. 27. The individual parts of the apparatus 100 are described more fully below.

In the apparatus 100 shown in FIG. 25, the preferred method of making the multi-layer female component 22 involves feeding the materials for the different zones or layers into the system and bonding the same. The materials may be bonded by various different methods, including, but not limited to by stitching, adhesives, ultrasonics, and by heat/pressure processes.

The preferred method of bonding the materials together is by passing the composite of the materials between two heated rolls, one of which has a pattern on its surface, and impressing the bond pattern into the materials. One method of heat/pressure bonding that could be used is described in U.S. Pat. No. 4,854,984 issued to Ball, et al. on Aug. 8, 1989 (provided the patterned cylinder described therein forms bonded areas that meet the criteria set forth in this description).

The first supply means 102 feeds a first material 118 used for the entanglement zone 30 into the system. The first material 118 can be any of those materials specified as being suitable for use in the entanglement zone 30 in Section 2 of this description. Thus, the first supply means 102 could be any conventional means used to introduce a material into a laminating process. The first supply means 102 could be, but is not limited to an unwind roll; a web or fabric producing machine, such as a conventional carding machine, spunbonding machine, loom, or knitting machine; or a hopper for feeding a layer of loose fibers into the system.

In the preferred embodiment of the process of the present invention, the first supply means 102 comprises either a supply of spunbonded fibers or a conventional machine for producing the same. Preferably, the first supply means 102 feeds a layer of loose (i.e., unbonded) continuous length fibers into the system. These fibers are, preferably, uniformly deposited onto a suitable surface. These fibers could be deposited onto a surface such as the material described below that will comprise the spacing zone 32.

In other alternative embodiments, rather than being in the form of a layer of loose fibers, the first material 118 could be in the form of a web of entangled fibers or a web of bonded fibers, a woven fabric, or the like.

Regardless of the form in which the first material is fed into the apparatus, (whether it be in the form of a web, or in the form of loose, unbonded fibers, etc.), the structural elements of the first material 118 are preferably oriented primarily in the machine direction when the first material 118 is introduced into the system. This will provide the female component 22 with structural elements having the desired single direction orientation that is preferred for holding the hooks of the mating hook component.

The term "machine direction" (MD) refers to that direction which is parallel to the flow of the materials 118, 120, and 122, through the apparatus 100. The "cross-machine direction" (CD) is perpendicular to the machine direction. These is directions are indicated by arrows in FIG. 25 and in several of the figures which follow.

The second supply means 104 feeds a second material 120, used for the spacing zone 32 into the system. The second material 120 can be any of those materials specified as being suitable for use in the spacing zone 32 in Section 2 of this description. Thus, the second supply means 104 could be any of the means used to introduce a material into a laminating process that were described above as being suitable for the first supply means 104.

In the preferred embodiment of the process of the present invention, the second supply means 104 comprises either a supply of carded fibers or a conventional carding machine. The second supply means 104, preferably feeds a layer of loose (i.e., unbonded), fibers into the system. The fibers are preferably randomly-oriented, crimped, and between about 2 and about 3 inches (between about 5 cm. to about 8 cm.) long. These fibers are preferably, uniformly deposited onto a suitable surface such as the third material described below that will comprise the backing 34.

In other alternative embodiments, rather than being in the form of layer of loose fibers, the second material 120 could be in the form of web of bonded fibers, a woven fabric, a screen, loose particles, or the like.

Preferably, the material 120 used in the spacing zone 32 will have sufficient thickness or loft built into its structure to accommodate the hooks of the mating hook component. If not, it is contemplated that the material 120 used to form the spacing zone 32 could be lofted during the process of making the female component. If that is the case, a means for lofting the second material could be included in the apparatus. Such a means could include a conventional pleating or corrugating process (represented by block 128 in FIG. 25). However, a process that requires such an extra step is generally less preferred.

With respect to the formation of the spacing zone 32, various alternatives embodiments of the process are possible.

Figure 26:
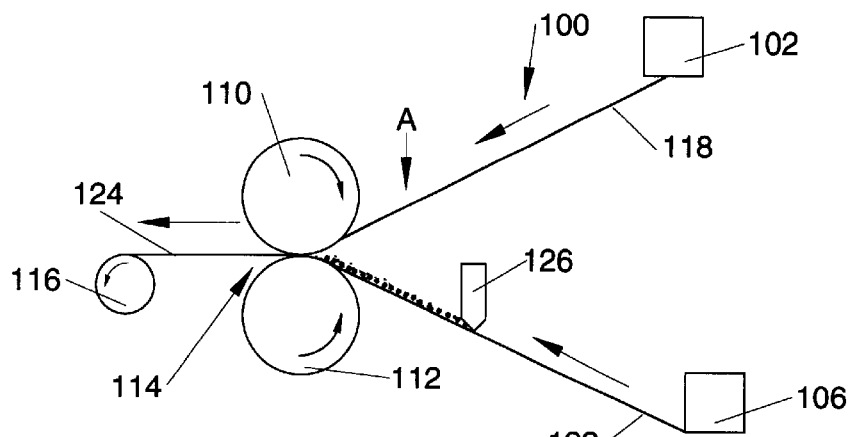
FIG. 26 is a schematic side view of an alternative process for making the multi-layer female component.

FIG. 26 shows an alternative embodiment of an apparatus that may be used if the material to be used as the spacing zone 32 is not a fibrous structure. (For example, the embodiment shown in FIG. 26 could be used if the material to be used in the spacing zone 32 is particulate.) In the embodiment shown in FIG. 26, the second supply means 104 is replaced by a hopper 126. The hopper 126 is disposed over the third material 122. The third material 122 serves as a surface upon which the loose material for the spacing zone 32 may be dispersed.

The third supply means 106 feeds a third material 122 into the system. The third material 122 is used for the backing 34. The third material 122 can be any of those materials specified as being suitable for use as the backing 34 in Section 2 of this description. The backing 34, as noted above, may be optional. If the backing 34 is eliminated, the function ordinarily served by the backing 34 may be performed by the substrate to which the female component 22 is attached. The third material 122 could, therefore, be a substrate, such as a material used for the backsheet of a disposable diaper.

Figure 27:
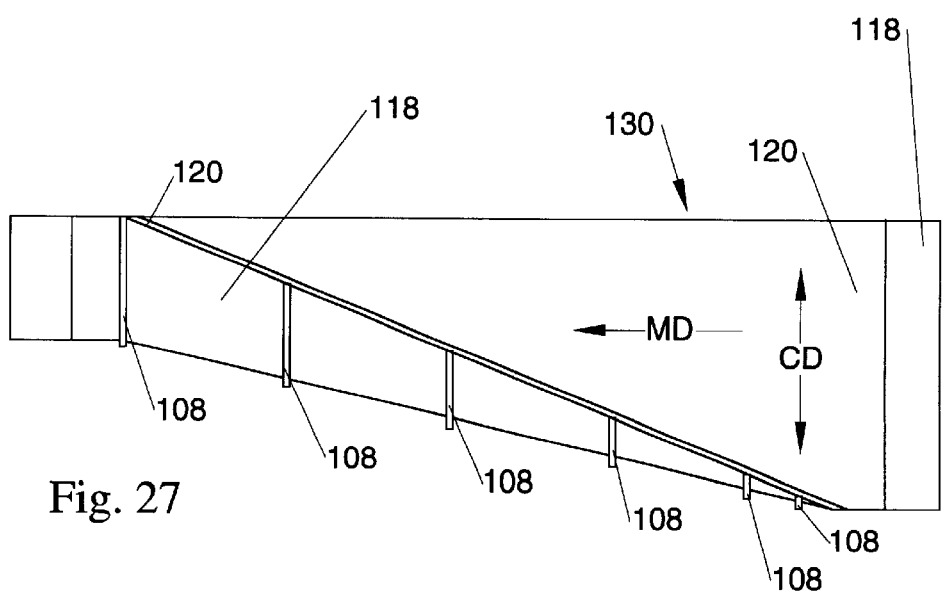
FIG. 27 shows an optional means for folding a web of material to form the multi-layer female component shown in FIGS. 12–17.

The optional folding bars 108 may be used to produce the folded embodiments of the female component 22, such as those shown in FIGS. 12–17. As discussed above, in such an embodiment, the film backing 34 is eliminated. As shown in FIG. 27, one of the materials generally used in the spacing zone 32, such as 120, can be placed on top of one of the materials generally used as the entanglement zone 30, such as 118, to form a laminate 130. The laminate 130 can then be folded over on top of itself to form the female component 22.

The overall process of making such a folded female component 22 can generally be represented schematically by FIG. 25. However, the materials fed into the system by the supply means are switched. Second material 120 is fed into the system by first supply means 102. First material 118 is fed into the system by second supply means 104. This will produce a laminate of the second material 120 on top of the first material 118. The third supply means 106 is eliminated. The optional folding bars 108 used in such a process are located before the nip 114. Preferably, the folding bars 108 are located at the place designated by reference letter A in FIGS. 25 and 26.

In other alternative embodiments, only one of the materials that forms the female component could be folded. Alternatively, more than one, but less than all of such materials (that is, at least one layer) could be folded. The folded material(s) could be the top layer, the bottom layer, or an intermediate layer or layers.

In still other alternative embodiments of the apparatus 100 shown in FIG. 25, additional optional supply means of similar configuration to those shown could be provided if it is desirable to construct a multi-layer female component with more than three layers.

The element that provides the embossed surface can be in any suitable configuration. For example, it can be in the form of an embossing plate or in the form of a cylinder. Preferably, it is a patterned cylinder, such as patterned cylinder 110. The patterned cylinder 110 is used to bond the layers of the multi-layer female component 22. The pattern forms the bonded areas 46 of the female component 22. The pattern should be in relief so that only a relatively small portion of the first and second materials will be compressed during the process. The remainder (particularly the remainder of the second material 120 which will form the spacing zone 32) should not be compressed so that the overall lofted character of the second material 120 will be maintained.

The pattern must form a bond with the characteristics described above. Thus, the space between the bonded areas 46 must be sufficient so that the hooks 28 of the mating hook component 24 can easily penetrate the entanglement and spacing zones 30 and 32. The space between the bonded areas 46 should not be too large, however. If, for instance, the space between bonded areas 46 is too large in relation to the length of the fibers used in a nonwoven entanglement zone 30, there will be an inordinate number of fibers with unbonded loose ends. The surface of the patterned roll 110 is shown in greater detail in FIG. 28.

The surface defines lands 132 and recesses 134. The lands 132 and recesses 134 of the roll 110 have several characteristics. These include roll depth or depth of the recesses, dimensions of the pattern, etc. These characteristics will vary depending on the materials used for the layers or zones of the female component 22 and on the type of bond pattern desired.

Figure 28:
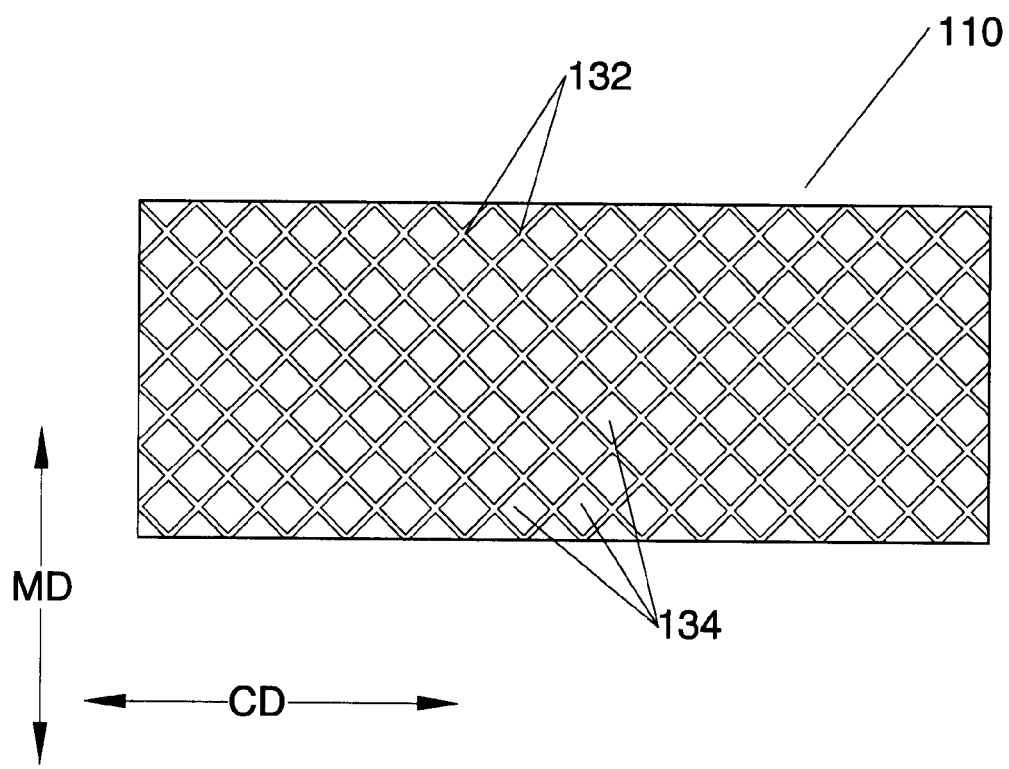
FIG. 28 is a schematic front view of one type of patterned roll that can be used in the processes shown in FIGS. 25 and 26 (the dimensions of the pattern being greatly enlarged for purposes of illustration).

The patterned roll 110 shown in FIG. 28 is used to form the preferred diamond-shaped bond pattern shown in FIGS. 1–3.

The depth of the recesses 134 (or the height of the lands 132) should generally be greater than the sum of the calipers of the first and second materials. Typically, the depth of the recesses is about 1½ times the sum of the calipers of these two materials.

The patterned roll 110 has lands 132 that are essentially square shapes that have been rotated approximately 45 degrees with respect to the cross machine direction. These squares can have any suitable dimensions. For instance, these squares can be ¼ inch×¼ inch (about 0.6 cm.×0.6 cm.); about ⅜ inch×⅜ inch (about 1 cm.×1 cm.); about ½ inch×½ inch (about 1.3 cm.×1.3 cm.); and, about ¾ inch×¾ inch (about 2 cm.×2 cm.) to form the bonds described in Section 2 above. The width of such lands 132 can, for example, be between about 0.03 inch and about 0.05 inch (about 0.76 mm. and about 1.3 mm.).

The embossed roll 110 may be, and preferably is, heated. The temperature to which the rolls, such as embossed roll 110, are heated depends on the materials used to form the layers of the female component 22. In the preferred embodiment shown, the first, second, and third materials are comprised of polypropylene. When polypropylene is used, the embossed roll 110 is preferably heated to a temperature of between about 155° C. and about 168° C.

The anvil member is preferably a cylinder with a smooth, surface, such as anvil roll 112. Preferably, the anvil roll 112 is also heated. Preferably, the anvil roll 112 is heated to a temperature of between about 104° C. and about 110° C. when polypropylene materials are used for the layers. The anvil roll 112 rotates in the opposite direction as the embossed roll 110 (in other words, the two rolls are counter-rotating).

The first, second, and third materials are bonded together when they pass through the nip 114. The materials for the three layers are bonded together by the application of heat and pressure from the rolls 110 and 112 at the nip 114. In one preferred embodiment of the process of the present invention, the rolls rotate so that the bonded web 124 is formed at a rate of about 100 feet/minute (about 30.5 meters/minute). The rolls exert a pressure of between about 300 and about 400 pounds per linear inch (between about 50 and about 70 kg./linear cm.) as measured across the nip in the cross-machine direction.

In alternative embodiments of the process of making the female component of the present invention, adhesives can be used to bond the layers together instead of heat or heat and pressure. In an adhesive bonding process, adhesive can be applied by any suitable commercial adhesive supply means 108. Preferably, the adhesive supply means applies adhesive in a pattern similar to that formed by the lands 132 of the patterned roll 110. In such adhesive bonding processes, the patterned roll 110 could be replaced with a second smooth roll. However, in most cases it is preferable that the patterned roll 110 still be used so that portions of the first and second materials 118 and 120 are not compressed and the lofted character of the second material 120 is maintained. Such adhesive bonding processes, could be conducted without the application of pressure. Preferably, however, in such cases pressure is also applied with the rolls.

In still other alternative embodiments, the rolls 110 and 112 could be replaced by a commercially available ultrasonic welding device.

The rewind roll 116 collects the bonded web 124 of female component material. The roll of female component material can be taken from the rewind roll 116 and can be cut into appropriate sizes for use in a refastenable fastening device with a suitable hook component. For example, the cut pieces of the female component material can be bonded onto a disposable diaper. In other alternative embodiments of the process of the present invention, the rewind roll 116 could be eliminated, and the bonded web 124 could be fed directly into the appropriate place of a diaper manufacturing line. The bonded web 124 could be cut and affixed directly to the appropriate places on a web of diaper material.

The multi-layer female component 22 can, thus, be made relatively inexpensively in comparison to conventional loop materials. This process eliminates the need to loft or manipulate material to form individual loops. This process also results in a lower cost female component because the female component can be produced by a lower cost and relatively straight-forward bonding or laminating process, rather than the conventional weaving, knitting, pleating, or corrugating processes.

While particular embodiments of the present invention have been illustrated and described, it would be obvious to those skilled in the art that various other changes and modifications can be made without departing from the spirit and scope of the invention. It is to be understood that all of the limits and ranges specified in the foregoing description of the fastening device include all narrower ranges and limits that are within the specified limits and ranges. Thus, for example if a range is specified as being between about 6 and about 42 g/m², all narrower ranges, such as between about 10 and about 40 g/m², and between about 20 and about 30 g/m², etc., may be claimed even though these ranges are not separately listed. It is therefore intended to cover in the appended Claims all such changes and modifications that are within the scope of this invention.

What is claimed is:

1. A multi-layer female component for a refastenable mechanical fastening device, said multi-layer female component comprising:

a first layer comprising a first nonwoven web having a basis weight of between about 8.5 and about 18 g/meter$^2$ comprised of fibers with a denier of between about 2 and about 15;

a second layer comprising a second nonwoven web having a basis weight of between about 8.5 and about 36 g meter$^2$ comprised of fibers with a denier of between about 2 and about 15; and a backing adjacent said second nonwoven web, wherein said first nonwoven web and said second nonwoven web are held in place with respect to said backing with said second nonwoven web in between said first nonwoven web and said backing, wherein said multi-layer female component is capable of engaging a hook component comprising a plurality of hooks, said hooks extending from a common integral planar base and having:

a base;

a stem supported at one end by the base;

a head having a beginning and a lowermost point, the beginning connected to the stem, the head projecting upwards from the stem and then downwards towards the base terminating at the lowermost point;

the head of the hook having a width (W), a height ($h^1$), a length (L) and a displacement volume, wherein the displacement volume is the volume of a rectangular parallelepiped having a bottom plane, first and second side planes, first and second end planes and a top plane; the bottom plane oriented parallel to the base and tangent to the lowermost point of the head, the top plane parallel to the apex of the hook, the side planes laying in the plane of the sides of the hook; the first end plane perpendicular to the bottom plane at a point where the bottom plane intersects the stem opposite from the lowermost point of the head, the second end plane perpendicular to the bottom plane and tangent to the portion of the head that is disposed farthest from the stem, wherein the displacement volume is less than or equal to about 0.03 mm$^3$.

2. The hook of claim 1 wherein the height ($h^1$) is less than or equal to about 0.3 mm.

3. The hook of claim 1 wherein the width (W) is less than or equal to about 0.2 mm.

4. The hook of claim 1 wherein the length (L) is less than or equal to about 0.5 mm.

5. The hook of claim 1 having a cross-section, wherein the hook tapers to decrease in cross-section from the base to the lowermost point.

* * * * *